US012570651B2

(12) United States Patent
Chilla et al.

(10) Patent No.: US 12,570,651 B2
(45) Date of Patent: Mar. 10, 2026

(54) QUINAZOLINE-2,4-DIONE DERIVATIVES AS PARP INHIBITORS

(71) Applicant: Suzhou Four Health Pharmaceuticals Co., Ltd., Taicang (CN)

(72) Inventors: Satya Chilla, Ans (BE); Corentin Warnier, Ans (BE); Thomas Vergote, Ans (BE); Jean-Luc Morelle, Ans (BE); Gauthier Philippart, Ans (BE)

(73) Assignee: Suzhou Four Health Pharmaceuticals Co., Ltd., Taicang Suzhou (CN)

( * ) Notice: Subject to any disclaimer, the term of this patent is extended or adjusted under 35 U.S.C. 154(b) by 1122 days.

(21) Appl. No.: 17/595,332

(22) PCT Filed: May 14, 2020

(86) PCT No.: PCT/EP2020/063453

§ 371 (c)(1),
(2) Date: Nov. 15, 2021

(87) PCT Pub. No.: WO2020/229595

PCT Pub. Date: Nov. 19, 2020

(65) Prior Publication Data

US 2022/0227757 A1 Jul. 21, 2022

(30) Foreign Application Priority Data

May 14, 2019 (EP) .................................... 19174456

(51) Int. Cl.

*C07D 471/04* (2006.01)
*A61P 35/00* (2006.01)
*C07D 401/06* (2006.01)
*C07F 5/02* (2006.01)

(52) U.S. Cl.

CPC ............ *C07D 471/04* (2013.01); *A61P 35/00* (2018.01); *C07D 401/06* (2013.01); *C07F 5/022* (2013.01)

(58) Field of Classification Search

None
See application file for complete search history.

(56) References Cited

FOREIGN PATENT DOCUMENTS

WO 2012125521 A1 9/2012
WO 2012130166 A1 10/2012

OTHER PUBLICATIONS

International Search Report issued Jun. 15, 2020 in PCT/EP2020/063453.
Written Opinion issued Jun. 15, 2020 in PCT/EP2020/063453.

*Primary Examiner* — Leslie A. Royds Draper
(74) *Attorney, Agent, or Firm* — Ice Miller LLP

(57) ABSTRACT

The present invention relates to compounds and compositions containing said compounds acting as PARP inhibitors (Poly (ADP-ribose) polymerase). Moreover, the present invention provides processes for the preparation of the disclosed compounds, as well as methods of using them, for instance as a medicine, in particular for the treatment of cell proliferative disorders, such as cancer.

11 Claims, 3 Drawing Sheets

QUINAZOLINE-2,4-DIONE DERIVATIVES AS PARP INHIBITORS

CROSS-REFERENCE TO RELATED APPLICATION

This application is a Section 371 of International Application No. PCT/EP2020/063453 filed May 14, 2020, which was published in the English language Nov. 19, 2020, under International Publication No. WO 2020/229595 A1, which claims priority to European Patent Application No. 2019174456 filed May 14, 2019, the disclosures of which are incorporated herein by reference in their entireties.

FIELD OF THE INVENTION

The present invention relates to compounds and compositions containing said compounds acting as PARP inhibitors (Poly (ADP-ribose) polymerase). Moreover, the present invention provides processes for the preparation of the disclosed compounds, as well as methods of using them, for instance as a medicine, in particular for the treatment of cell proliferative disorders, such as cancer.

BACKGROUND TO THE INVENTION

The nuclear enzyme poly(ADP-ribose) polymerase-1 (PARP-1) is a member of the PARP enzyme family. PARP-1 and PARP-2 are unique members of the family, in that their catalytic activities are stimulated by the occurrence of DNA strand breaks. PARP plays a role in DNA repair mechanisms, through its ability to recognize and rapidly bind to DNA single or double strand breaks. Therefore, PARP inhibition is a valuable tool in cancer treatment and diagnosis thereof.

PARP inhibition can be especially effective when combined with DNA damaging treatment, such as with ionizing radiation or after treatment with DNA damaging agents. The inhibition of PARP enzymatic activity leads to an enhanced sensitivity of the tumor cells towards DNA damaging treatments.

Certain small molecules have been reported to be PARP inhibitors. For example, PCT Publication Nos: WO2000/42040 and 2004/800713 report tricyclic indole derivatives as PARP inhibitors. PCT Publication Nos. WO 2002/44183 and 2000/105700 report tricyclic diazepinoindole derivatives as PARP inhibitors PCT Publication No. WO 2011/130661 and GB patent 2462361 report dihydropyridophthalazinone derivatives as PARP inhibitors. Moreover, some publications report on radiolabeled and fluorescent labeled PARP inhibitors for use in imaging and/or radiotherapy (e.g. WO2018218025).

However, there is a continuous need for further PARP inhibitory molecules suitable in the diagnosis and/or treatment of cancer. Thereto, this patent family provides compounds and/or pharmaceutically acceptable salts thereof; pharmaceutical compositions comprising at least one of those compounds and pharmaceutically acceptable salts thereof and use thereof in inhibiting PARP activity for diagnosing and/or treating diseases such as cancer. For example, the compounds and compositions as described herein can be useful in treating cancers with defective DNA repair pathways and/or can be useful in enhancing the effectiveness of chemotherapy and radiotherapy.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

SUMMARY OF THE INVENTION

Figure 1:
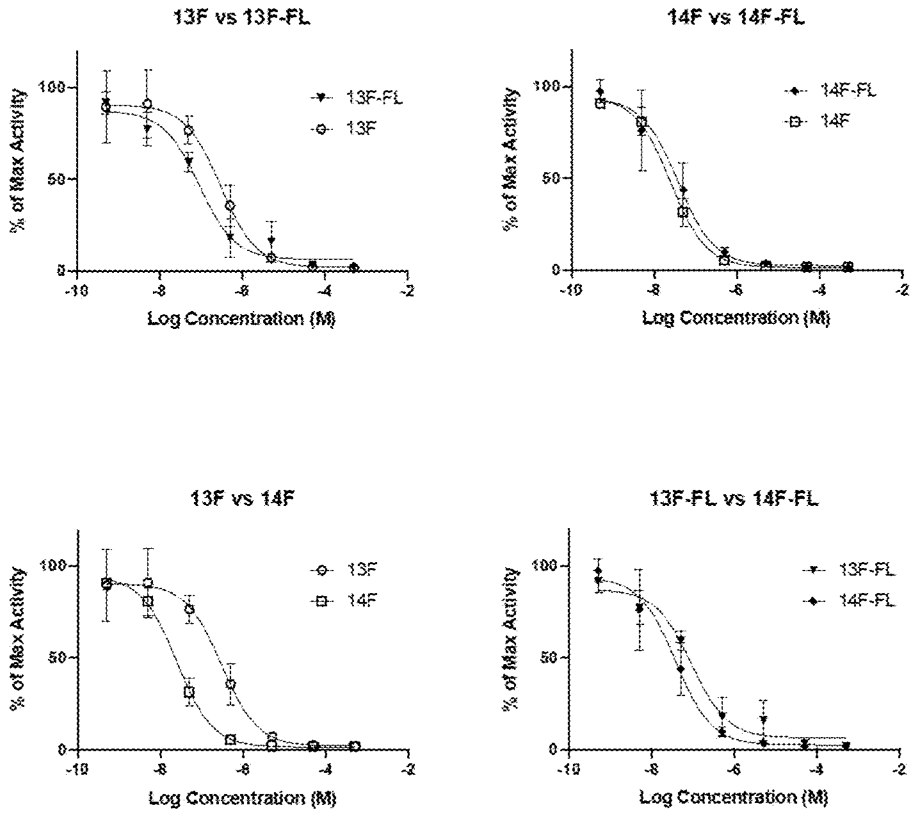
FIG. 1: Dose-response inhibition curves used to determine $IC_{50}$-values of different PARP-inhibitors.

In a first aspect, the present invention provides a compound of Formula I or a stereoisomer, tautomer, racemic, salt, hydrate, solvate, or isotope thereof, (I)

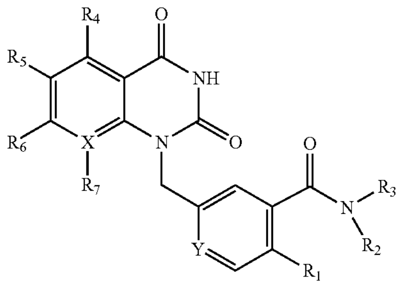

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl;

X and Y are each independently selected from C and N;

wherein at least one of said X and Y is N;

wherein when X is N then $R_7$ is absent.

In a particular embodiment, the present invention provides a compound as defined herein; more in particular being of Formula II or a stereoisomer, tautomer, racemic, salt, hydrate, solvate, or isotope thereof, (II)

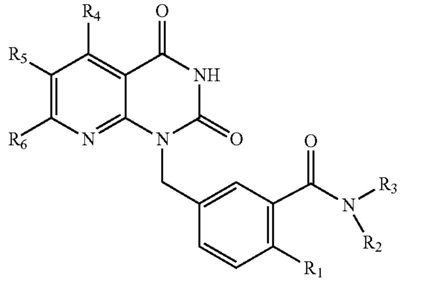

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, and $R_6$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl.

In yet a further particular embodiment, the present invention provides a compound as defined herein; more in particular being of Formula III or a stereoisomer, tautomer, racemic, hydrate, solvate, or isotope thereof, (III)

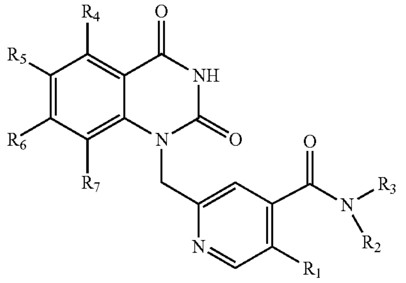

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-20}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl.

In another particular embodiment, the present invention provides a compound of formula I, II or III; wherein:

$R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, —C(═O)$R_8$, —O—$R_8$, —$R_8$, and -aminoalkyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -cyano, —C(═O)$R_8$, -carboxy, -ester, -amino, -amido, -acylamido, -ureido, and -acyloxy;

wherein said bicyclic heterocylic moiety may be a spiro-moiety;

$R_4$, $R_5$, $R_6$ and $R_7$ are each independently selected from the list comprising —H, and -halogen;

or $R_7$ is absent when said compound is in accordance with formula (II);

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl.

In a specific embodiment, the present invention provides a compound as defined herein, such as being of formula I, II or III;

wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In another specific embodiment, the present invention provides a compound as defined herein, such as being of formula I, II or III; wherein at least one of said $R_1$, $R_4$, $R_5$, $R_6$ and $R_7$ is a radioactive halogen selected from the list comprising $^{18}$F and $^{123}$I, preferably $^{18}$F.

In another very specific embodiment, the present invention provides a compound as defined herein, such as being of formula I, II or III;

wherein $R_2$ and $R_3$ taken together with the N atom to which they are attached form a piperazine moiety; which is further substituted with at least one substituent selected from the list comprising: a fluorescent moiety, —$C_{1-20}$alkyl, —$C_{1-20}$alkenyl, —$C_{1-20}$alkynyl, —$C_{1-20}$ cycloalkyl, —$C_{5-20}$aryl, —$C_{5-20}$heteroaryl, —$C_{3-20}$ heterocyclyl, -amido, -thioamido, -ester, -aminoalkyl, —C(═O)$R_8$, —O—$R_8$, —$R_8$, and -sulfonyl groups; and wherein either $R_8$ is a fluorescent moiety, or at least one of said substituent of $R_2$ and $R_3$ is further substituted with a fluorescent moiety;

In yet another specific embodiment, the present invention provides a compound as defined herein and being selected from the following list; wherein each Z is independently selected from —I, —Br, —At and —F; each of said —I, —Br, —At and —F being optionally radiolabeled:

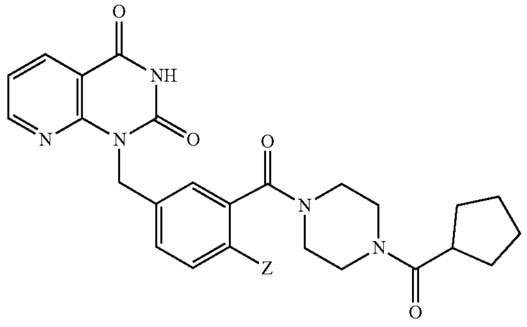

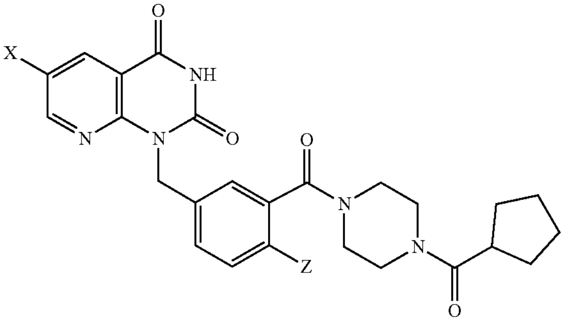

-continued

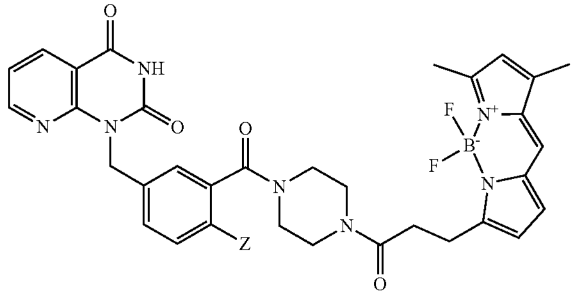

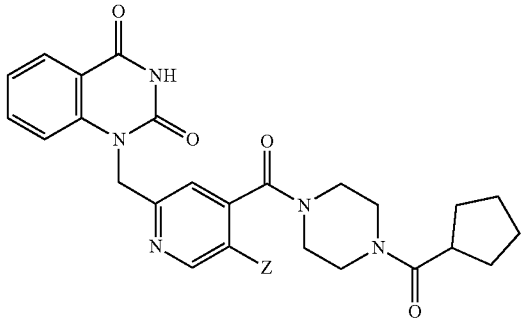

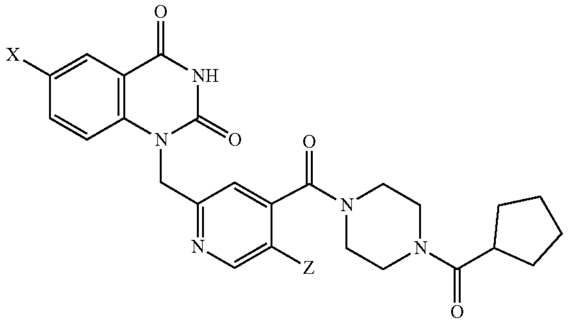

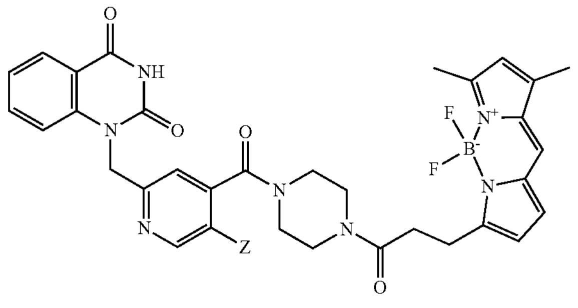

The present invention further provides a compound of Formula I or a stereoisomer, tautomer, racemic, salt, hydrate, solvate, or isotope thereof, and being selected from the list comprising:

-continued

Compound 1

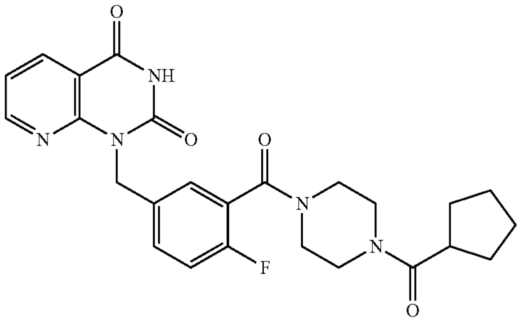

Compound 2

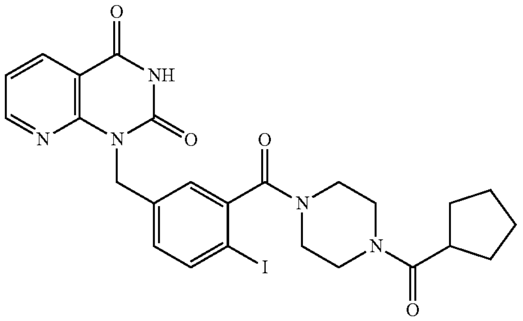

Compound 3

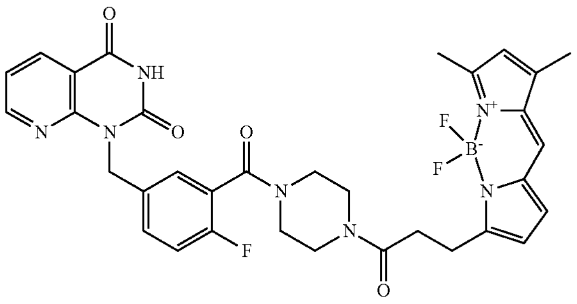

Compound 4

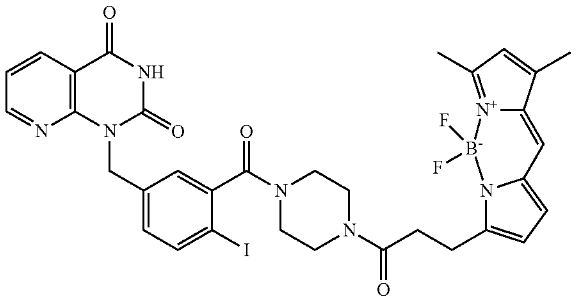

Compound 5

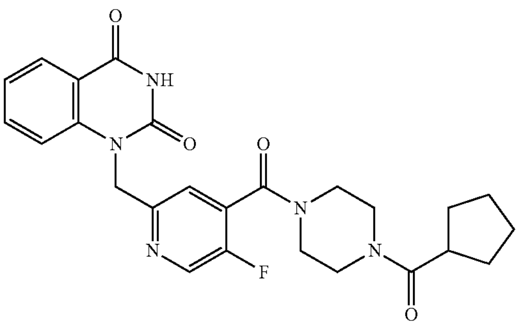

Compound 6

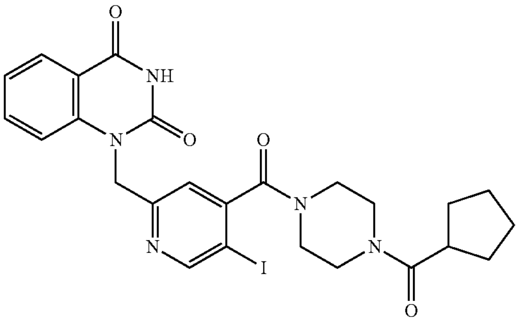

Compound 7

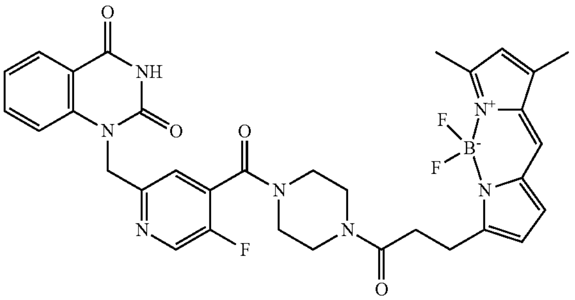

Compound 8

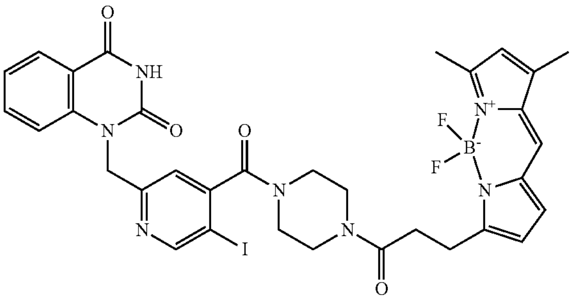

In each of the above defined compounds, one or more of the indicated halogen atoms may optionally be replaced by a radiolabeled one, such as —F may be replaced by $^{18}$F; I may be replaced by $^{123}$I, . . . .

The present invention further provides a pharmaceutical composition comprising a compound as defined herein; more in particular being of formula I, II or III; and a pharmaceutically acceptable diluent, acceptable carrier, or excipient, adjuvant or vehicle.

The present invention further provides a compound as defined herein; or a pharmaceutical composition comprising such compound; for use in human or veterinary medicine;

more in particular for use in the diagnosis or treatment of a disorder characterized by PARP (Poly (ADP-ribose) polymerase) overexpression; such as for example selected from list comprising: breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

Finally, the present invention provides the use of compound as defined herein; or a pharmaceutical composition comprising such compound; in the in vivo imaging of PARP distribution.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides a compound of Formula I or a stereoisomer, tautomer, racemic, salt, hydrate, solvate, or isotope thereof, (I)

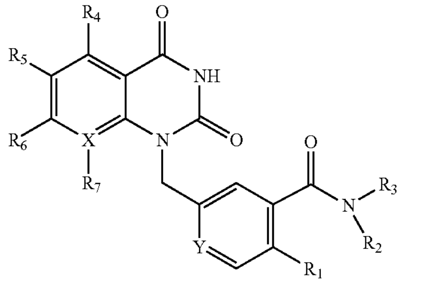

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(=O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(=O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl;

wherein at least one of said X and Y is N;

wherein when X is N then $R_7$ is absent.

When describing the compounds of the invention, the terms used are to be construed in accordance with the following definitions, unless a context dictates otherwise:

The term "alkyl" by itself or as part of another substituent refers to a fully saturated hydrocarbon of Formula $C_xH_{2x+1}$ wherein x is a number greater than or equal to 1. Generally, alkyl groups of this invention comprise from 1 to 20 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers, heptyl and its isomers, octyl and its isomers, nonyl and its isomers; decyl and its isomers. $C_1$-$C_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopentyl, 2-, 3-, or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3, or 4 substituents or 1 to 2 substituents) at any available point of attachment. Non-limiting examples of such substituents include a fluorescent moiety, —$C_{1-20}$alkyl, —$C_{5-20}$aryl, —$C_{3-20}$heterocyclyl, -halo, -hydroxy, -ether, -nitro, -cyano, —C(=O)$R_8$, -carboxy, -ester, -amino, -amido, -acylamido, -ureido, -acyloxy, -thiol, -thioether, -sulfoxide, -sulfonyl, -thioamido and -sulfonamino and the like.

The term "alkenyl", as used herein, unless otherwise indicated, means straight-chain, cyclic, or branched-chain hydrocarbon radicals containing at least one carbon-carbon double bond. Examples of alkenyl radicals include ethenyl, E- and Z-propenyl, isopropenyl, E- and Z-butenyl, E- and Z-isobutenyl, E- and Z-pentenyl, E- and Z-hexenyl, E,E-, E,Z-, Z,E-, Z,Z-hexadienyl, and the like. An optionally substituted alkenyl refers to an alkenyl having optionally one or more substituents (for example 1, 2, 3 or 4), selected from those defined above for substituted alkyl.

The term "alkynyl", as used herein, unless otherwise indicated, means straight-chain or branched-chain hydrocarbon radicals containing at least one carbon-carbon triple bond. Examples of alkynyl radicals include ethynyl, E- and Z-propynyl, isopropynyl, E- and Z-butynyl, E- and Z-isobutynyl, E- and Z-pentynyl, E, Z-hexynyl, and the like. An optionally substituted alkynyl refers to an alkynyl having optionally one or more substituents (for example 1, 2, 3 or 4), selected from those defined above for substituted alkyl.

The term "cycloalkyl" by itself or as part of another substituent is a cyclic alkyl group, that is to say, a monovalent, saturated, or unsaturated hydrocarbyl group having 1, 2, or 3 cyclic structure. Cycloalkyl includes all saturated or partially saturated (containing 1 or 2 double bonds) hydrocarbon groups containing 1 to 3 rings, including monocyclic, bicyclic, or polycyclic alkyl groups. Cycloalkyl groups may comprise 3 or more carbon atoms in the ring and generally, according to this invention comprise from 3 to 15 atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups include but are not limited to cyclopropyl, cyclobutyl, cyclopentyl, cyclohexyl, cycloheptyl, cyclooctyl, cyclononyl, adamantanyl and cyclodecyl with cyclopropyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

The terms "heterocyclyl" or "heterocycle" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, . . . ; preferably piperidinyl.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 6 to 10 atoms; wherein at least one ring is aromatic. The aromatic ring may optionally include one to three additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, . . . .

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from selected from those defined above for substituted alkyl, alkylsulfoxide, $—SO_2R^a$, alkylthio, carboxyl, and the like, wherein $R^a$ is alkyl or cycloalkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyrrolyl, furanyl, thiophenyl, pyrazolyl, imidazolyl, . . . .

An "optionally substituted heteroaryl" refers to a heteroaryl having optionally one or more substituents (for example 1 to 4 substituents, for example 1, 2, 3 or 4), selected from those defined above for substituted alkyl.

The term "oxo" as used herein refers to the group =O.

The term "alkoxy" or "alkyloxy" as used herein refers to a radical having the Formula $—OR^b$ wherein $R^b$ is alkyl. Preferably, alkoxy is $C_1$-$C_{10}$ alkoxy, $C_1$-$C_6$ alkoxy, or $C_1$-$C_4$ alkoxy. Non-limiting examples of suitable alkoxy include methoxy, ethoxy, propoxy, isopropoxy, butoxy, isobutoxy, sec-butoxy, tert-butoxy, pentyloxy and hexyloxy. Where the oxygen atom in an alkoxy group is substituted with sulfur, the resultant radical is referred to as thioalkoxy.

The term "aryloxy" as used herein denotes a group —O-aryl, wherein aryl is as defined above.

The term "arylcarbonyl" or "aroyl" as used herein denotes a group —C(O)-aryl, wherein aryl is as defined above.

The term "carboxy" or "carboxyl" or "hydroxycarbonyl" by itself or as part of another substituent refers to the group $—CO_2H$. Thus, a carboxyalkyl is an alkyl group as defined above having at least one substituent that is $—CO_2H$.

The term "alkoxy" by itself or as part of another substituent refers to a group consisting of an oxygen atom attached to one optionally substituted straight or branched alkyl group, cycloalkyl group, aralkyl, or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy, and the like.

The term "halo" or "halogen" as a group or part of a group is generic for fluorine, chlorine, bromine, iodine, or astatine.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

Where groups may be optionally substituted, such groups may be substituted with once or more, and preferably once, twice or thrice. Substituents may be selected from, for example, the group comprising halogen, hydroxyl, oxo, nitro, amido, carboxy, amino, cyano haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

As described herein, some of the compounds of the invention may contain one or more asymmetric carbon atoms that serve as a chiral center, which may lead to different optical forms (e.g. enantiomers or diastereoisomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

Whenever used in the present invention the term "compounds of the invention" or a similar term is meant to include the compounds of general Formula I and any subgroup thereof. This term also refers to the compounds as depicted in Tables 1 to 11, their derivatives, N-oxides, salts, solvates, hydrates, stereoisomeric forms, racemic mixtures, tautomeric forms, optical isomers, analogues, and esters, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above, and others used in the specification are well understood to those in the art.

In a particular embodiment, the present invention provides a compound as defined herein, in particular of Formula (I) (II) or (III) or a stereoisomer, tautomer, racemic, salt, hydrate, solvate, or isotope thereof, wherein $R_1$ is halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, and —C(═O)$R_8$; each of these further optionally substituted with one or more substituents selected from the list comprising a fluorescent moiety, —$C_{3-20}$heterocyclyl, and -carboxy;

$R_4$, $R_5$, $R_6$ and $R_7$ are each —H;

$R_8$ is selected from the list comprising a fluorescent moiety, —$C_{1-20}$alkyl, and —$C_{1-20}$cycloalkyl; X and Y are each independently selected from C and N;

wherein at least one of said X and Y is N;

wherein when X is N then $R_7$ is absent.

In a particular embodiment, the present invention provides a compound as defined herein, or a stereoisomer, tautomer, racemic, salt, hydrate, solvate, or isotope thereof, wherein $R_1$ is halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, and —C(═O)$R_8$; each of these further optionally substituted with one or more substituents selected from the list comprising a fluorescent moiety, —$C_{3-20}$heterocyclyl, and -carboxy;

$R_4$, $R_5$, and $R_6$ are each —H;

$R_8$ is selected from the list comprising a fluorescent moiety, —$C_{1-20}$alkyl, and —$C_{1-20}$cycloalkyl;

X is N;

Y is C; and $R_7$ is absent.

In a particular embodiment, the present invention provides a compound as defined herein, or a stereoisomer, tautomer, racemic, salt, hydrate, solvate, or isotope thereof, wherein $R_1$ is halogen;

$R_2$ and $R_3$ taken together with the N atom to which they are attached, represent a piperazine moiety; substituted with —$C_{1-20}$alkyl; which may further optionally be substituted with one or more substituents selected from the list comprising a fluorescent moiety, —$C_{3-20}$heterocyclyl, and -carboxy;

$R_4$, $R_5$, and $R_6$ are each —H;

X is N;

Y is C; and $R_7$ is absent.

In a particular embodiment, the present invention provides a compound as defined herein, or a stereoisomer, tautomer, racemic, salt, hydrate, solvate, or isotope thereof, wherein $R_1$ is —F or —I; preferably —F;

$R_2$ and $R_3$ taken together with the N atom to which they are attached, represent a piperazine moiety; substituted with —$C_{1-20}$alkyl; which may further optionally be substituted with one or more substituents selected from the list comprising a fluorescent moiety, —$C_{3-20}$heterocyclyl, and -carboxy;

$R_4$, $R_5$, and $R_6$ are each —H;

X is N;

Y is C; and $R_7$ is absent.

In a particular embodiment, the present invention provides a compound as defined herein, or a stereoisomer, tautomer, racemic, salt, hydrate, solvate, or isotope thereof, wherein $R_1$ is halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, and —C(═O)$R_8$; each of these further optionally substituted with one or more substituents selected from the list comprising a fluorescent moiety, —$C_{3-20}$heterocyclyl, and -carboxy;

$R_4$, $R_5$, $R_6$ and $R_7$ are each —H;

$R_8$ is selected from the list comprising a fluorescent moiety, —$C_{1-20}$alkyl, and —$C_{1-20}$cycloalkyl;

X is C; and

Y is N.

In a particular embodiment, the present invention provides a compound as defined herein, or a stereoisomer, tautomer, racemic, salt, hydrate, solvate, or isotope thereof, wherein $R_1$ is halogen;

$R_2$ and $R_3$ taken together with the N atom to which they are attached, represent a piperazine moiety; substituted with —$C_{1-20}$alkyl; which may further optionally be substituted with one or more substituents selected from the list comprising a fluorescent moiety, —$C_{3-20}$heterocyclyl, and -carboxy;

$R_4$, $R_5$, $R_6$ and $R_7$ are each —H;

X is C; and

Y is N.

In a particular embodiment, the present invention provides a compound as defined herein, or a stereoisomer, tautomer, racemic, salt, hydrate, solvate, or isotope thereof, wherein $R_1$ is —F or —I; preferably —F;

$R_2$ and $R_3$ taken together with the N atom to which they are attached, represent a piperazine moiety; substituted with —$C_{1-20}$alkyl; which may further optionally be substituted with one or more substituents selected from the list comprising a fluorescent moiety, —$C_{3-20}$heterocyclyl, and -carboxy;

$R_4$, $R_5$, $R_6$ and $R_7$ are each —H;

X is C; and

Y is N.

The compounds of the present invention are particularly suitable for several applications, depending on the type of substituents used:

Therapeutic cold compounds

Therapeutic radiolabeled compounds

Diagnostic radiolabeled compounds

Diagnostic fluorescently labeled compounds

Therapeutic Cold Compounds

Compounds of the present invention may be used for therapeutic applications, wherein said compounds are in a 'cold' format, i.e. they are not labeled such as they are not radiolabeled nor fluorescently labeled.

Hence, the present invention provides a compound of Formula I or a stereoisomer, tautomer, racemic, salt, hydrate, or solvate thereof, (I)

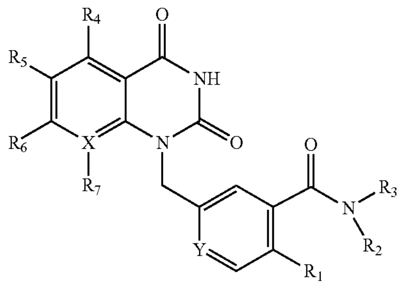

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2\ 0}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl;

X and Y are each independently selected from C and N;

wherein at least one of said X and Y is N;

wherein when X is N then $R_7$ is absent; and wherein said compound does not contain a radioactive or fluorescent moiety.

In a particular embodiment, the present invention provides a compound as defined herein; more in particular being of Formula II or a stereoisomer, tautomer, racemic, salt, hydrate, or solvate thereof, (II)

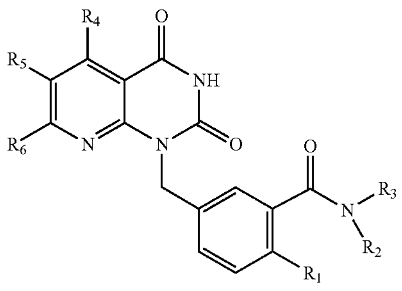

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, and $R_6$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl;

and wherein said compound does not contain a radioactive or fluorescent moiety.

In yet a further particular embodiment, the present invention provides a compound as defined herein; more in particular being of Formula III or a stereoisomer, tautomer, racemic, salt, hydrate, or solvate thereof, (III)

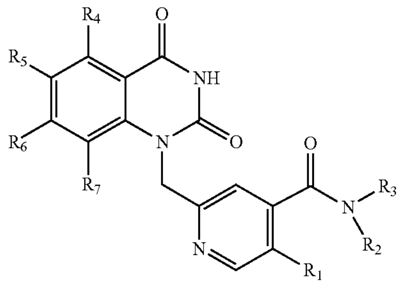

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(=O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2\ 0}$heterocyclyl, -halo, -hydroxy, -ether, -nitro, -cyano, —C(=O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl;

and wherein said compound does not contain a radioactive or fluorescent moiety.

In another particular embodiment, the present invention provides a compound of formula I, II or III; wherein:

$R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, —C(=O)$R_8$, —O—$R_8$, —$R_8$, and -aminoalkyl groups; each of these further optionally substituted with a substituent selected from the list comprising —$C_{1-2\ 0}$alkyl, —$C_{5-20}$aryl, —$C_{3-20}$heterocyclyl, -halo, -hydroxy, -ether, -cyano, —C(=O)$R_8$, -carboxy, -ester, -amino, -amido, -acylamido, -ureido, and -acyloxy;

wherein said bicyclic heterocylic moiety may be a spiro-moiety;

$R_4$, $R_5$, $R_6$ and $R_7$ are each independently selected from the list comprising —H, and -halogen;

or $R_7$ is absent when said compound is in accordance with formula (II);

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein said compound does not contain a radioactive or fluorescent moiety.

In a particular embodiment, the present invention provides a compound of Formula I or a stereoisomer, tautomer, racemic, salt, hydrate, or solvate thereof, (I)

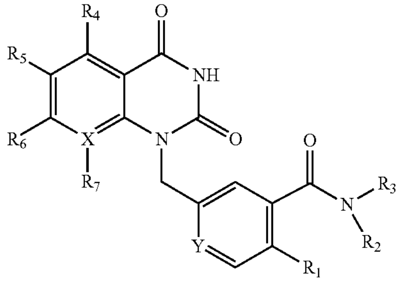

wherein $R_1$ is halogen;

$R_2$ and $R_3$ taken together with the N atom to which they are attached, represent a piperazine moiety; which is further substituted with —C(=O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; X and Y are each independently selected from C and N;

at least one of said X and Y is N; wherein when X is N then $R_7$ is absent; and wherein said compound does not contain a radioactive or fluorescent moiety.

In a particular embodiment, the present invention provides a compound of Formula II or a stereoisomer, tautomer, racemic, salt, hydrate, or solvate thereof, (II)

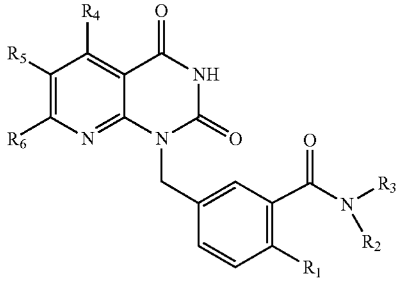

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein said compound does not contain a radioactive or fluorescent moiety.

In a particular embodiment, the present invention provides a compound of Formula III or a stereoisomer, tautomer, racemic, salt, hydrate, or solvate thereof, (III)

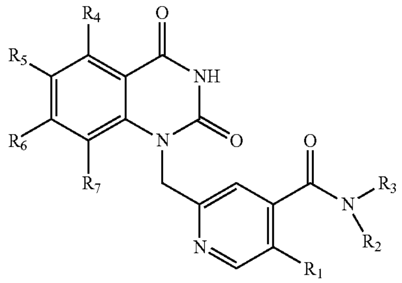

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein said compound does not contain a radioactive or fluorescent moiety.

In yet another specific embodiment, the present invention provides a compound as defined herein and being selected from the following list; wherein each Z is independently selected from non-radiolabeled —I, —Br, —At and —F:

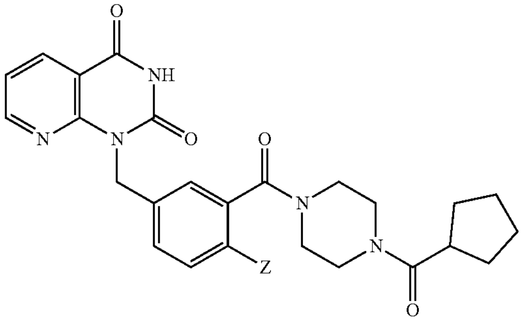

-continued

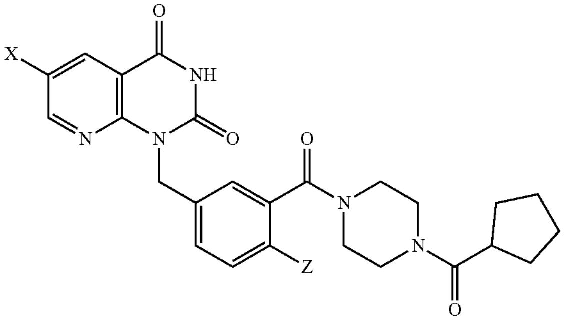

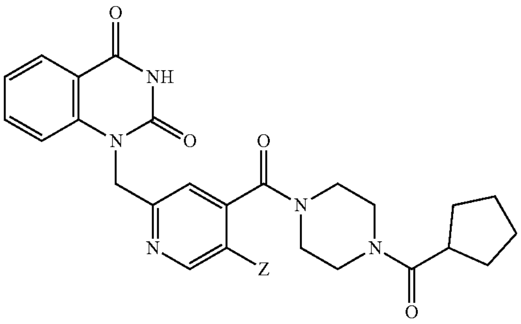

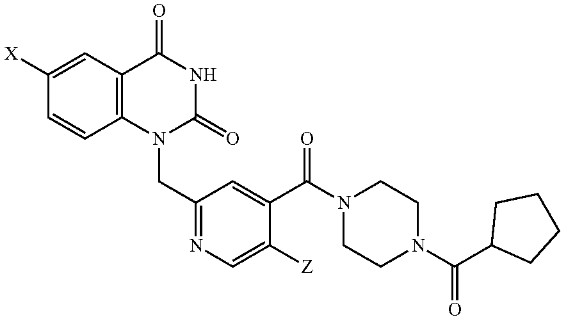

In a very specific embodiment, the present invention provides a compound as defined herein, and being selected from the list comprising:

Compound 1

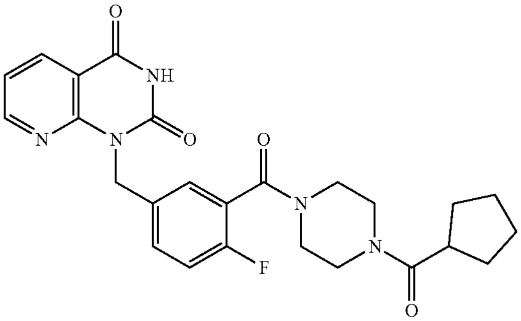

-continued

Compound 2

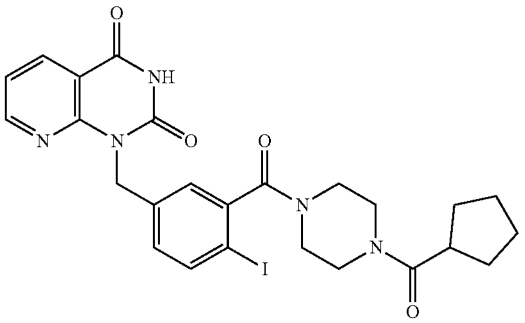

Compound 5

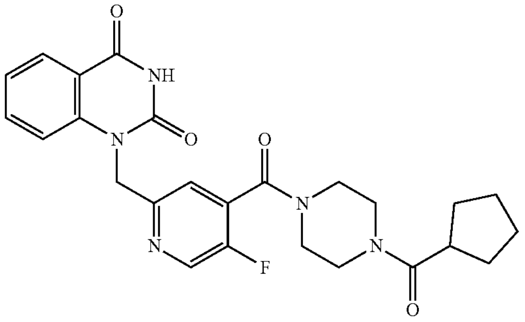

Compound 6

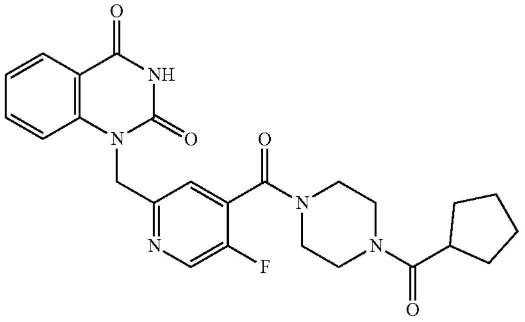

The present invention further provides a pharmaceutical composition comprising a compound as defined herein; more in particular being of formula I, II or III; and a pharmaceutically acceptable diluent, acceptable carrier, or excipient, adjuvant or vehicle.

The present invention further provides a compound as defined herein; or a pharmaceutical composition comprising such compound; for use in human or veterinary medicine; more in particular for use in the treatment of a disorder characterized by PARP (Poly (ADP-ribose) polymerase) overexpression; such as for example selected from list comprising: breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

Therapeutic Radiolabeled Compounds

Compounds of the present invention may be used for radio-therapeutic applications, wherein said compounds are radioactively labeled.

Hence, the present invention provides a compound of Formula I or a stereoisomer, tautomer, racemic, salt, hydrate, solvate, or isotope thereof, (I)

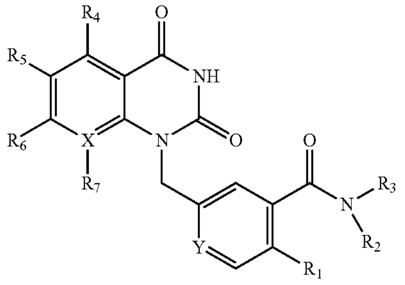

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-20}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl;

X and Y are each independently selected from C and N;

wherein at least one of said X and Y is N;

wherein when X is N then $R_7$ is absent; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In a particular embodiment, the present invention provides a compound as defined herein; more in particular being of Formula II or a stereoisomer, tautomer, racemic, salt, hydrate, solvate, or isotope thereof, (II)

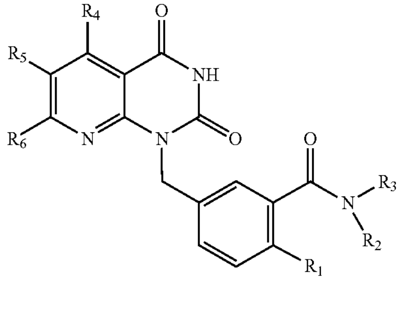

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2\ 0}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, and $R_6$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In yet a further particular embodiment, the present invention provides a compound as defined herein; more in particular being of Formula III or a stereoisomer, tautomer, racemic, salt, hydrate, solvate, or isotope thereof, (III)

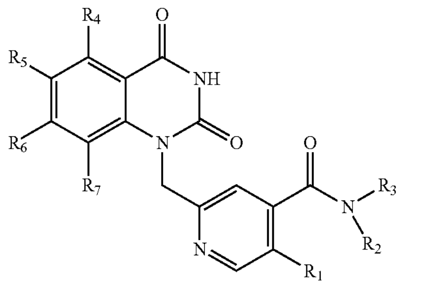

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2\ 0}$ heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, $R_6$ and $R_7$ are each independently selected from the list comprising —H, -halogen -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In another particular embodiment, the present invention provides a compound of formula I, II or III; wherein:

$R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, —C(═O)$R_8$, —O—$R_8$, —$R_8$, and -aminoalkyl groups; each of these further optionally substituted with a substituent selected from the list comprising —$C_{1-20}$alkyl, —$C_{5-20}$aryl, —$C_{3-20}$heterocyclyl, -halo, -hydroxy, -ether, -cyano, —C(═O)$R_8$, -carboxy, -ester, -amino, -amido, -acylamido, -ureido, and -acyloxy;

wherein said bicyclic heterocylic moiety may be a spiro-moiety;

$R_4$, $R_5$, $R_6$ and $R_7$ are each independently selected from the list comprising —H, and -halogen;

or $R_7$ is absent when said compound is in accordance with formula (II);

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In a particular embodiment, the present invention provides a compound of Formula I or a stereoisomer, tautomer, racemic, salt, hydrate, solvate or isotope thereof, (I)

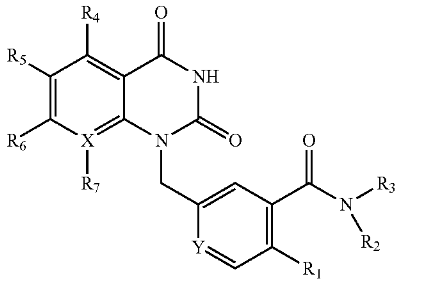

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; X and Y are each independently selected from C and N;

at least one of said X and Y is N; wherein when X is N then $R_7$ is absent; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In a particular embodiment, the present invention provides a compound of Formula II or a stereoisomer, tautomer, racemic, salt, hydrate, solvate or isotope thereof, (II)

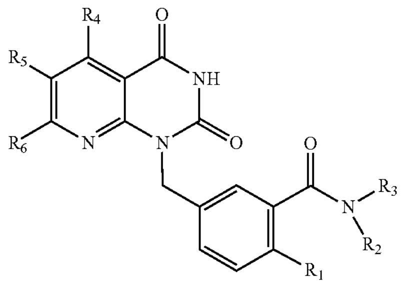

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In a particular embodiment, the present invention provides a compound of Formula III or a stereoisomer, tautomer, racemic, salt, hydrate, solvate or isotope thereof, (III)

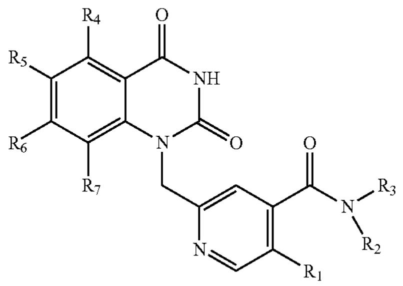

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is a radioactive halogen selected from the list comprising $^{76}$Br, $^{77}$Br, $^{81}$Br, $^{123}$I, $^{125}$I, $^{131}$I, $^{209}$At, $^{210}$At, and $^{211}$At.

In yet another specific embodiment, the present invention provides a compound as defined herein and being selected from the following list; wherein each Z is independently selected from —I, —Br, —At and —F; and at least one of said X is selected from $^{76}$Br, $^{77}$Br, $^{81}$Br, $^{123}$I, $^{125}$I, $^{131}$I, $^{209}$At, $^{210}$At, and $^{211}$At

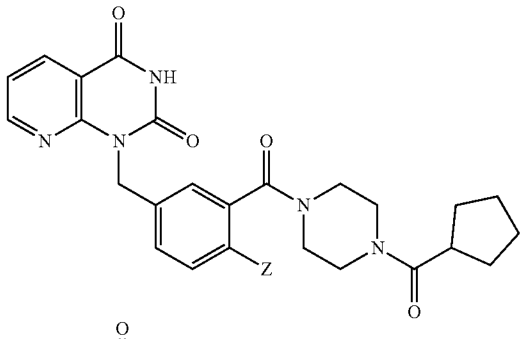

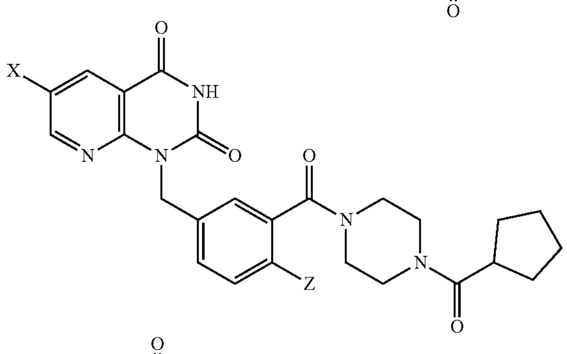

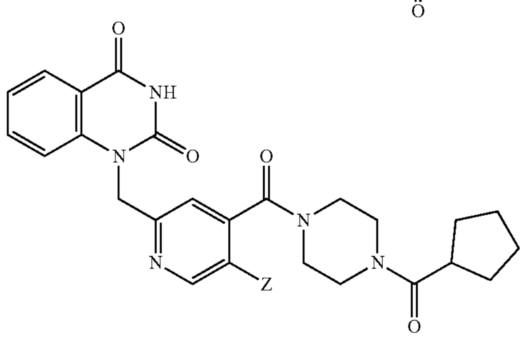

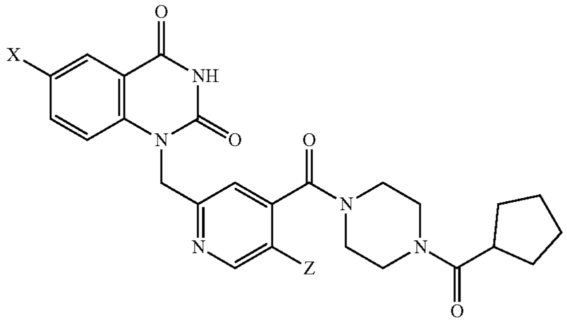

In a very specific embodiment, the present invention provides a compound as defined herein, and being selected from the list comprising:

Compound 2

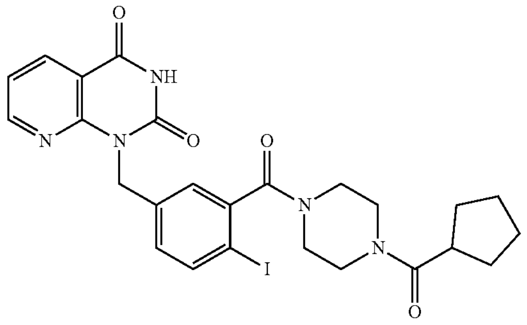 [SMILES: O=C(c1cc(Cn2c(=O)[nH]c(=O)c3cccnc32)ccc1I)N1CCN(C(=O)C2CCCC2)CC1]

Compound 6

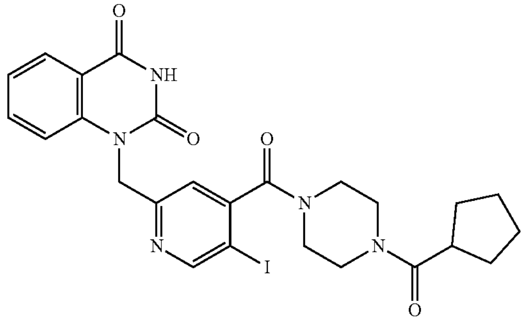

In each of the above defined compounds, one or more of the indicated halogen atoms may optionally be replaced by a radiolabeled one, such as I may be replaced by $^{123}I$, $^{125}I$, $^{131}I$, . . . .

The present invention further provides a pharmaceutical composition comprising a compound as defined herein; more in particular being of formula I, II or III; and a pharmaceutically acceptable diluent, acceptable carrier, or excipient, adjuvant or vehicle.

The present invention further provides a compound as defined herein; or a pharmaceutical composition comprising such compound; for use in human or veterinary medicine; more in particular for use in the treatment of a disorder characterized by PARP (Poly (ADP-ribose) polymerase) overexpression; such as for example selected from list comprising: breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

Diagnostic Radiolabeled Compounds

Compounds of the present invention may be used for diagnostic applications, wherein said compounds are radiolabeled.

Hence, the present invention provides a compound of Formula I or a stereoisomer, tautomer, racemic, salt, hydrate, solvate, or isotope thereof, (I)

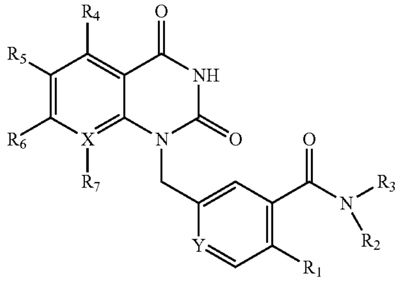

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(=O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2}$ 0heterocyclyl, -halo, -hydroxy, -ether, -nitro, -cyano, —C(=O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl;

X and Y are each independently selected from C and N;

wherein at least one of said X and Y is N;

wherein when X is N then $R_7$ is absent; and wherein at least one of said $R_1$, $R_4$, $R_5$, $R_6$ and $R_7$ is selected from $^{18}F$ and $^{123}I$; preferably $^{18}F$.

In a particular embodiment, the present invention provides a compound as defined herein; more in particular being of Formula II or a stereoisomer, tautomer, racemic, salt, hydrate, solvate, or isotope thereof, (II)

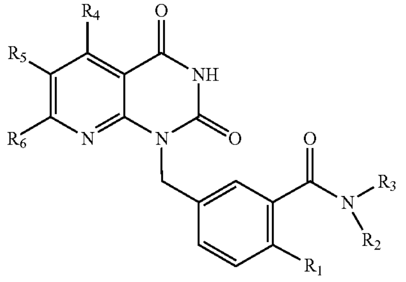

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2\ 0}$ heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, and $R_6$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, - carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl;

and wherein at least one of said $R_1$, $R_4$, $R_5$, $R_6$ and $R_7$ is selected from $^{18}F$ and $^{123}I$; preferably $^{18}F$.

In yet a further particular embodiment, the present invention provides a compound as defined herein; more in particular being of Formula III or a stereoisomer, tautomer, racemic, salt, hydrate, solvate, or isotope thereof, (III)

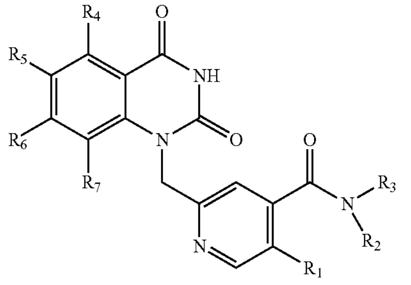

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising —$C_{1-20}$alkyl, —$C_{5-20}$aryl, —$C_{3-2\ 0}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, - thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is selected from $^{18}F$ and $^{123}I$; preferably $^{18}F$.

In another particular embodiment, the present invention provides a compound of formula I, II or III; wherein:

$R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, —C(═O)$R_8$, —O—$R_8$, —$R_8$, and -aminoalkyl groups; each of these further optionally substituted with a substituent selected from the list comprising —$C_{1-20}$alkyl, —$C_{5-20}$aryl, —$C_{3-20}$heterocyclyl, -halo, -hydroxy, -ether, -cyano, —C(═O)$R_8$, -carboxy, -ester, -amino, -amido, -acylamido, -ureido, and -acyloxy;

wherein said bicyclic heterocylic moiety may be a spiro-moiety;

$R_4$, $R_5$, $R_6$ and $R_7$ are each independently selected from the list comprising —H, and -halogen; or $R_7$ is absent when said compound is in accordance with formula (II);

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is selected from $^{18}F$ and $^{123}I$; preferably $^{18}F$.

In a particular embodiment, the present invention provides a compound of Formula I or a stereoisomer, tautomer, racemic, salt, hydrate, solvate or isotope thereof, (I)

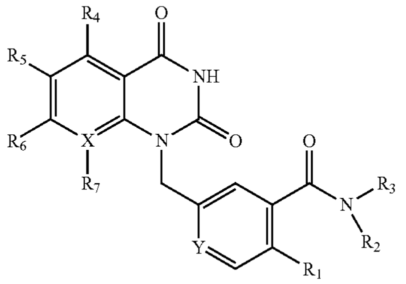

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; X and Y are each independently selected from C and N;

at least one of said X and Y is N; wherein when X is N then $R_7$ is absent; and wherein at least one of said $R_1$, $R_4$, $R_5$, $R_6$ and $R_7$ is selected from $^{18}$F and $^{123}$I; preferably $^{18}$F.

In a particular embodiment, the present invention provides a compound of Formula II or a stereoisomer, tautomer, racemic, salt, hydrate, solvate or isotope thereof, (II)

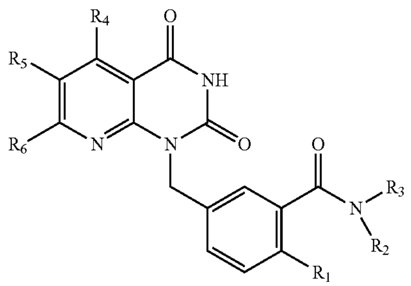

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is selected from $^{18}$F and $^{123}$I; preferably $^{18}$F.

In a particular embodiment, the present invention provides a compound of Formula III or a stereoisomer, tautomer, racemic, salt, hydrate, solvate or isotope thereof, (III)

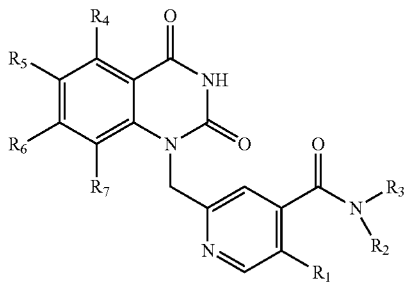

wherein $R_1$ is halogen;

$R_2$ and $R_3$ taken together with the N atom to which they are attached, represent a piperazine moiety; which is further substituted with —C(═O)$R_8$;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein at least one of said $R_1$, $R_4$, $R_5$, $R_6$ and $R_7$ is selected from $^{18}$F and $^{123}$I; preferably $^{18}$F.

In yet another specific embodiment, the present invention provides a compound as defined herein and being selected from the following list; wherein each Z is independently selected from —I, —Br, —At and —F; and at least one of said Z is $^{18}$F or $^{123}$I; preferably $^{18}$F:

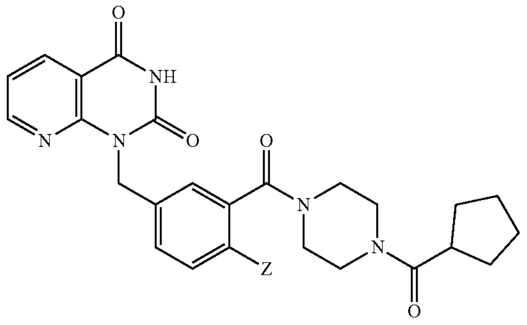

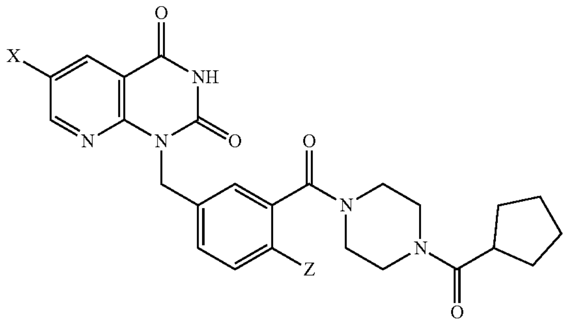

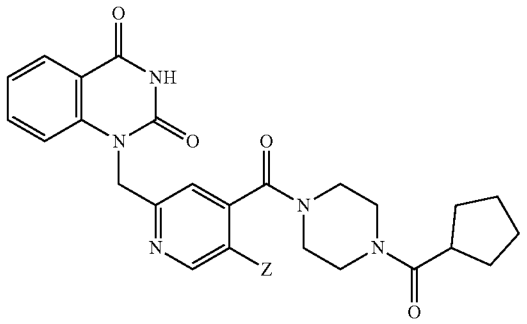

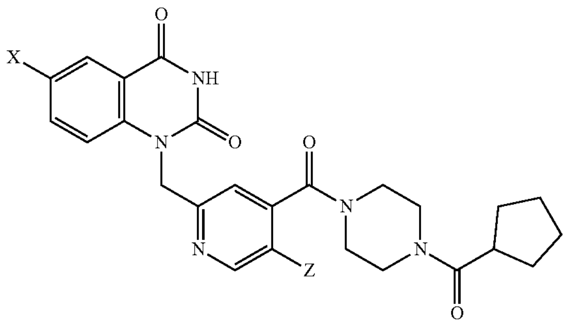

In a very specific embodiment, the present invention provides a compound as defined herein, and being selected from the list comprising:

Compound 1

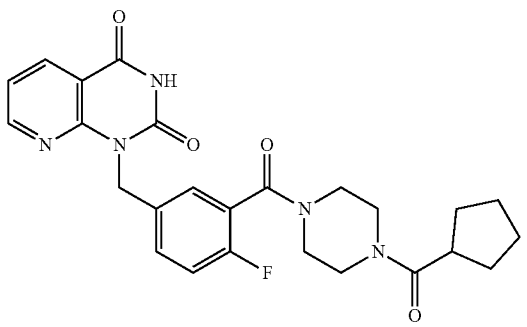

Compiound 5

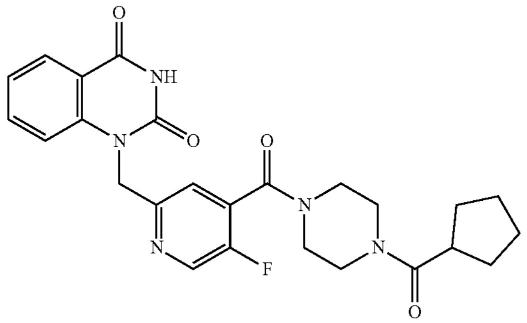

In each of the above defined compounds, one or more of the indicated halogen atoms may optionally be replaced by a radiolabeled one, such as —F may be replaced by $^{18}$F.

The present invention further provides a pharmaceutical composition comprising a compound as defined herein; more in particular being of formula I, II or III; and a pharmaceutically acceptable diluent, acceptable carrier, or excipient, adjuvant or vehicle.

The present invention further provides a compound as defined herein; or a pharmaceutical composition comprising such compound; for use in human or veterinary medicine; more in particular for use in the diagnosis of a disorder characterized by PARP (Poly (ADP-ribose) polymerase) overexpression; such as for example selected from list comprising: breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

Finally, the present invention provides the use of compound as defined herein; or a pharmaceutical composition comprising such compound; in the in vivo imaging of PARP distribution.

Diagnostic Fluorescently Labeled Compounds

Compounds of the present invention may be used for diagnostic applications, wherein said compounds are fluorescently labeled.

Hence, the present invention provides a compound of Formula I or a stereoisomer, tautomer, racemic, salt, hydrate, or solvate thereof, (I)

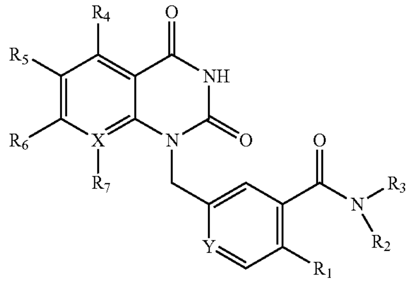

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl;

X and Y are each independently selected from C and N;

wherein at least one of said X and Y is N;

wherein when X is N then $R_7$ is absent; and wherein either $R_8$ is a fluorescent moiety, or at least one of said substituent of $R_2$ and $R_3$ is further substituted with a fluorescent moiety.

In a particular embodiment, the present invention provides a compound as defined herein; more in particular being of Formula II or a stereoisomer, tautomer, racemic, salt, hydrate, or solvate thereof, (II)

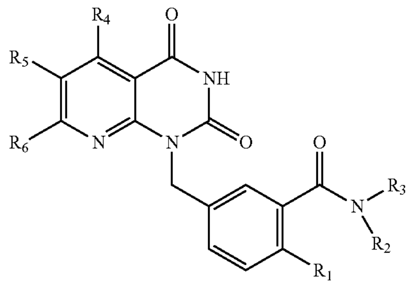

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, and $R_6$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl and wherein either $R_8$ is a fluorescent moiety, or at least one of said substituent of $R_2$ and $R_3$ is further substituted with a fluorescent moiety;

In yet a further particular embodiment, the present invention provides a compound as defined herein; more in particular being of Formula III or a stereoisomer, tautomer, racemic, salt, hydrate, or solvate thereof,

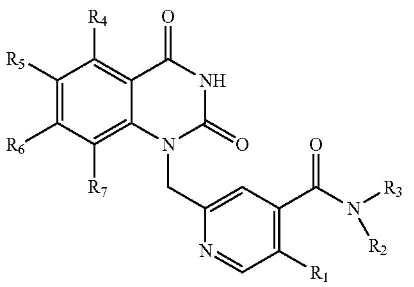

(III)

wherein $R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, -aminoalkyl, —C(═O)$R_8$, —O—$R_8$, —$R_8$, and -sulfonyl groups; each of these further optionally substituted with a substituent selected from the list comprising a fluorescent moiety, —$C_{1-20}$alkyl, —$C_{5-20}$aryl, —$C_{3-20}$heterocyclyl, -halo, -hydroxy, -ether, -nitro, -cyano, —C(═O)$R_8$, -carboxy, -ester, -amino, -amido, -acylamido, -ureido, -acyloxy, -thiol, -thioether, -sulfoxide, -sulfonyl, -thioamido and -sulfonamino;

wherein said bicyclic heterocylic moiety may be a spiro-moiety;

$R_4$, $R_5$, $R_6$ and $R_7$ are each independently selected from the list comprising —H, -halogen, -amino, -alkoxy, —$C_{1-10}$ alkyl, —$C_{1-20}$alkenyl, —$C_{1-20}$alkynyl, -haloalkyl, -hydroxyalkyl, -aminoalkyl, -carboxyalkyl, -ethylenedioxo, -nitro, -cyano, -acylamido, -hydroxy, -thiol, -acyloxy, -azido, -carboxy, -carbonylamido and -alkylthiol;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl and wherein either $R_8$ is a fluorescent moiety, or at least one of said substituent of $R_2$ and $R_3$ is further substituted with a fluorescent moiety.

In another particular embodiment, the present invention provides a compound of formula I, 11 or III; wherein:

$R_1$ is selected from the list comprising —H, and halogen;

$R_2$ and $R_3$ taken together with the N atom to which they are attached, represent a 5-10 membered mono- or bicyclic heterocyclic moiety; which may further be optionally substituted with a substituent selected from the list comprising: —$C_{1-20}$alkyl, —$C_{1-20}$alkenyl, —$C_{1-20}$alkynyl, —$C_{1-20}$cycloalkyl, —$C_{5-20}$aryl, —$C_{5-2\ 0}$heteroaryl, —$C_{3-20}$heterocyclyl, -amido, -thioamido, -ester, —C(═O)$R_8$, —O—$R_8$, —$R_8$, and -aminoalkyl groups; each of these further optionally substituted with a substituent selected from the list comprising a fluorescent moiety, —$C_{1-20}$alkyl, —$C_{5-2\ 0}$aryl, —$C_{3-20}$heterocyclyl, -halo, -hydroxy, -ether, -cyano, —C(═O)$R_8$, -carboxy, -ester, -amino, -amido, -acylamido, -ureido, and -acyloxy;

wherein said bicyclic heterocylic moiety may be a spiro-moiety;

$R_4$, $R_5$, $R_6$ and $R_7$ are each independently selected from the list comprising —H, and -halogen;

or $R_7$ is absent when said compound is in accordance with formula (II);

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl; and wherein either $R_8$ is a fluorescent moiety, or at least one of said substituent of $R_2$ and $R_3$ is further substituted with a fluorescent moiety.

In a particular embodiment, the present invention provides a compound of Formula I or a stereoisomer, tautomer, racemic, salt, hydrate, or solvate thereof,

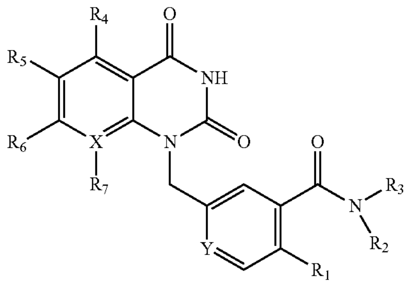

(I)

wherein $R_1$ is halogen;

$R_2$ and $R_3$ taken together with the N atom to which they are attached, represent a piperazine moiety; which is further substituted with a moiety selected from —$C_{1-20}$alkyl, —$C_{1-20}$alkenyl, —$C_{1-20}$alkynyl, —$C_{1-20}$ cycloalkyl, —$C_{5-20}$aryl, —$C_{5-20}$heteroaryl, —$C_{3-20}$ heterocyclyl, -amido, -thioamido, -ester, —C(═O)$R_8$, —O—$R_8$, —$R_8$, and -aminoalkyl groups;

$R_4$, and $R_6$ are —H $R_5$ is selected from —H and -halogen;

$R_8$ is selected from the list comprising —H, a fluorescent moiety, —$C_{1-20}$alkyl, —$C_{1-20}$cycloalkyl, —$C_{3-20}$heterocyclyl, —$C_{5-20}$aryl, —$C_{5-20}$heteroaryl; X and Y are each independently selected from C and N;

at least one of said X and Y is N; wherein when X is N then $R_7$ is absent; and wherein either $R_8$ is a fluorescent moiety, or at least one of said piperazine substituents is further substituted with a fluorescent moiety.

In a particular embodiment, the present invention provides a compound of Formula II or a stereoisomer, tautomer, racemic, salt, hydrate, or solvate thereof, (II)

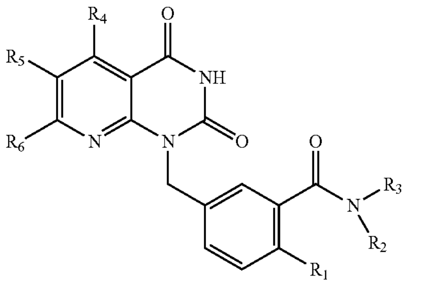

wherein $R_1$ is halogen;

$R_2$ and $R_3$ taken together with the N atom to which they are attached, represent a piperazine moiety; which is further substituted with a moiety selected from —$C_{1-20}$alkyl, —$C_{1-20}$alkenyl, —$C_{1-20}$alkynyl, —$C_{1-20}$ cycloalkyl, —$C_{5-20}$aryl, —$C_{5-20}$heteroaryl, —$C_{3-20}$heterocyclyl, -amido, -thioamido, -ester, —C(═O)$R_8$, —O—$R_8$, —$R_8$, and -aminoalkyl groups;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein either $R_8$ is a fluorescent moiety, or at least one of said piperazine substituents is further substituted with a fluorescent moiety.

In a particular embodiment, the present invention provides a compound of Formula III or a stereoisomer, tautomer, racemic, salt, hydrate, or solvate thereof, (III)

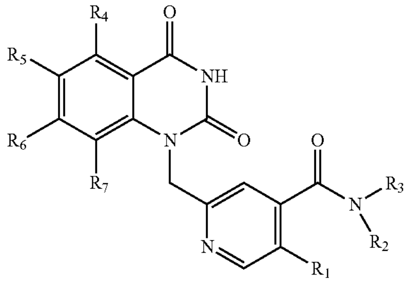

wherein $R_1$ is halogen;

$R_2$ and $R_3$ taken together with the N atom to which they are attached, represent a piperazine moiety; which is further substituted with a moiety selected from —$C_{1-20}$alkyl, —$C_{1-20}$alkenyl, —$C_{1-20}$alkynyl, —$C_{1-20}$ cycloalkyl, —$C_{5-20}$aryl, —$C_{5-20}$heteroaryl, —$C_{3-20}$ heterocyclyl, -amido, -thioamido, -ester, —C(═O)$R_8$, —O—$R_8$, —$R_8$, and -aminoalkyl groups;

$R_4$, and $R_6$ are —H $R_5$ is selected from —H and -halogen;

$R_8$ is selected from the list comprising —H, —$C_{1-20}$alkyl, —$C_{1-20}$cycloalkyl, —$C_{3-20}$heterocyclyl, —$C_{5-20}$aryl, —$C_{5-20}$heteroaryl; and wherein either $R_8$ is a fluorescent moiety, or at least one of said piperazine substituents is further substituted with a fluorescent moiety.

In a specific embodiment of the present invention, the fluorescent moiety may be a BODIPY Fluorophore. Particularly interesting fluorescent moieties are the BODIPY Succinimidyl Esters, such as:

BODIPY FL $C_3$ succinimidyl ester
BODIPY FL $C_5$ succinimidyl ester
BODIPY R6G $C_3$ succinimidyl ester
BODIPY 493/503 $C_3$ succinimidyl ester
BODIPY 530/550 $C_3$ succinimidyl ester
BODIPY 558/568 $C_3$ succinimidyl ester
BODIPY 564/570 $C_3$ succinimidyl ester
BODIPY 576/589 $C_3$ succinimidyl ester
BODIPY 581/591 $C_3$ succinimidyl ester
BODIPY FL-X succinimidyl ester
BODIPY TMR-X succinimidyl ester
BODIPY TR-X succinimidyl ester
BODIPY 630/650-X succinimidyl ester
BODIPY 650/665-X succinimidyl ester In yet another specific embodiment, the present invention provides a compound as defined herein and being selected from the following list; wherein each Z is independently selected from a non-radioactive —I, —Br, and —F:

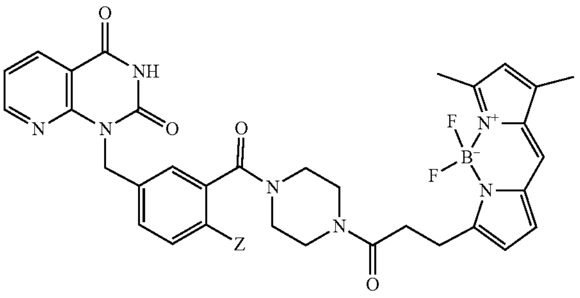

-continued

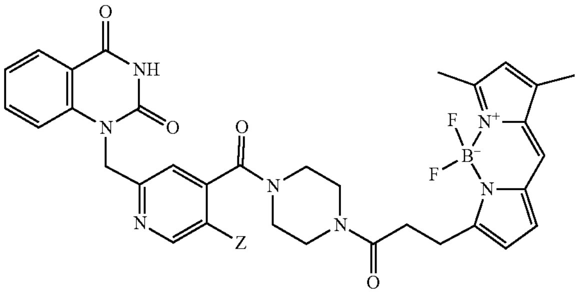

In a very specific embodiment, the present invention provides a compound as defined herein, and being selected from the list comprising:

Compound 3

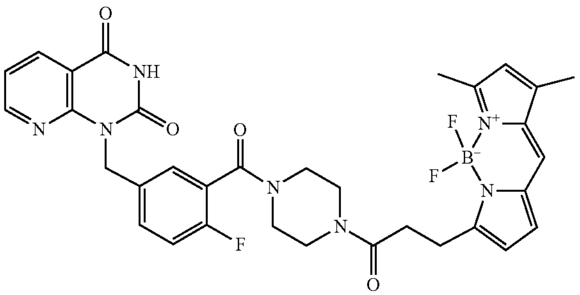

Compound 4

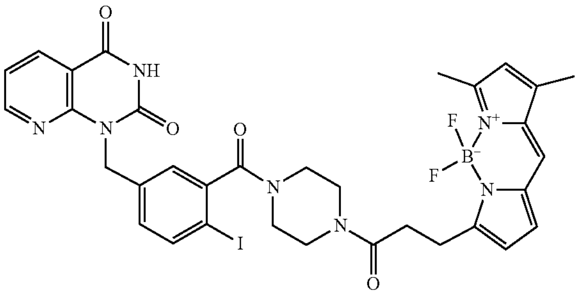

Compound 7

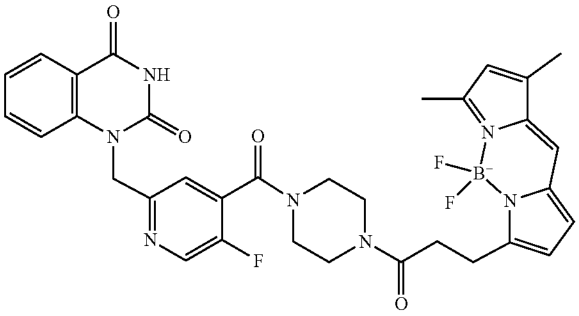

-continued

Compound 8

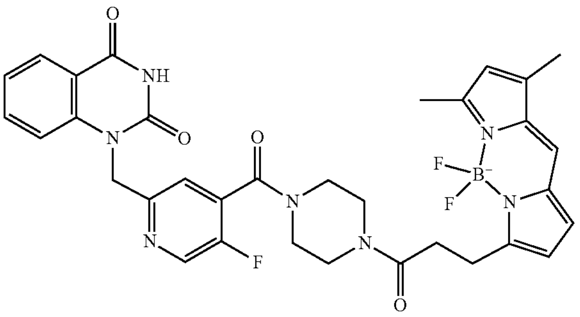

The present invention further provides a pharmaceutical composition comprising a compound as defined herein; more in particular being of formula I, II or III; and a pharmaceutically acceptable diluent, acceptable carrier, or excipient, adjuvant or vehicle.

The present invention further provides a compound as defined herein; or a pharmaceutical composition comprising such compound; for use in human or veterinary medicine; more in particular for use in the diagnosis of a disorder characterized by PARP (Poly (ADP-ribose) polymerase) overexpression; such as for example selected from list comprising: breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

Finally, the present invention provides the use of compound as defined herein; or a pharmaceutical composition comprising such compound; in the in vivo imaging of PARP distribution.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

Method of Treatment or Diagnosis

As detailed herein above, depending on the selection of substituents, the compounds of the present invention may be suitable for use in the diagnosis, prevention and/or treatment of disorders characterized by PARP (Poly (ADP-ribose) polymerase) overexpression; such as for example selected from list comprising: breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

In a particular embodiment, the compounds of the present invention may be suitable for use in the diagnosis, prevention and/or treatment of oral carcinoma, esophageal cancer, skin cancer, malignant wounds (e.g. breast wounds, colon wounds, prostate wounds, . . . ), and lung disorders. For both types of carcinoma, i.e. oral carcinoma and esophageal cancer, the subcategories squamous cell carcinoma as well as adenocarcinoma fall within the intended scope. In particular, the fluorescently labeled compounds of the present invention are highly suitable in the diagnosis of these disorders.

Wherever in this application, the term "pharmaceutical use" is used, this is meant to include both therapeutic as well as diagnostic uses of the (labeled) compounds of the invention.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 6,372,778, 6,369,086, 6,369,087.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use (diagnosis, prevention or treatment), the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

In respect of the diagnostic applications specifically, the compounds may be formulated as a solution for use as a mouthwash or (esophageal) spray. Measurements may then for example be taken endoscopically.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. An interesting way of formulating the compounds in combination with a cyclodextrin or a derivative thereof has been described in EP-A-721,331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

Particular reference is made to the compositions, formulations (and carriers, excipients, diluents, etc. for use therein), routes of administration etc., which are known per se for analogous pyridinocarboxamides, such as those described in U.S. Pat. No. 4,997,834 and EP-A-0 370 498.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof. The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,369,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I, II or III or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used locally, for instance topical or in both absorbed and non-adsorbed applications.

The compositions are of value in the veterinary field, which for the purposes herein not only includes the prevention and/or treatment of diseases in animals, but also—for economically important animals such as cattle, pigs, sheep, chicken, fish, etc.—enhancing the growth and/or weight of the animal and/or the amount and/or the quality of the meat or other products obtained from the animal. Thus, in a further aspect, the invention relates to a composition for veterinary use that contains at least one compound of the invention and at least one suitable carrier (i.e. a carrier suitable for veterinary use). The invention also relates to the use of a compound of the invention in the preparation of such a composition.

The invention will now be illustrated by means of the following synthetic and biological examples, which do not limit the scope of the invention in any way.

EXAMPLES

General Experimental Details

Yields reported herein refer to purified products (unless specified). Analytical TLC was performed on Merck silica gel 60 F254 aluminium-backed plates. Compounds were visualised by UV light and/or stained with iodine, ninhydrin or potassium permanganate solution followed by heating. Flash column chromatography was performed on silica gel. 1H-NMR spectra were recorded on a Bruker 400 MHz, Avance II spectrometer with a 5 mm DUL (Dual) 13C probe and Bruker 400 MHz, Avance III HD spectrometer with BBFO (Broad Band Fluorine Observe) probe. Chemical shifts (6) are expressed in parts per million (ppm) with reference to the deuterated solvent peak in which the sample is prepared. Splitting patterns are designated as s (singlet), d (doublet), t (triplet), q (quartet), m (multiplet) and br s (broad singlet).

The following solvents, reagents or scientific terminology may be referred to by their abbreviations:

TLC Thin Layer Chromatography
mL Milliliters
mmol Millimoles
h Hour or hours
min Minute or minutes
g Grams
mg Milligrams
eq Equivalents
rt or RT Room temperature, ambient, about 25° C.
MS Mass spectrometry A. Synthesis Schemes A.1. Compound Synthesis The compounds of the invention may be prepared by methods well known to those skilled in the art, and as described in the synthetic and experimental procedures shown below.

Synthesis of Compounds of Formula II

Example 1a: TRA-13F Synthesis

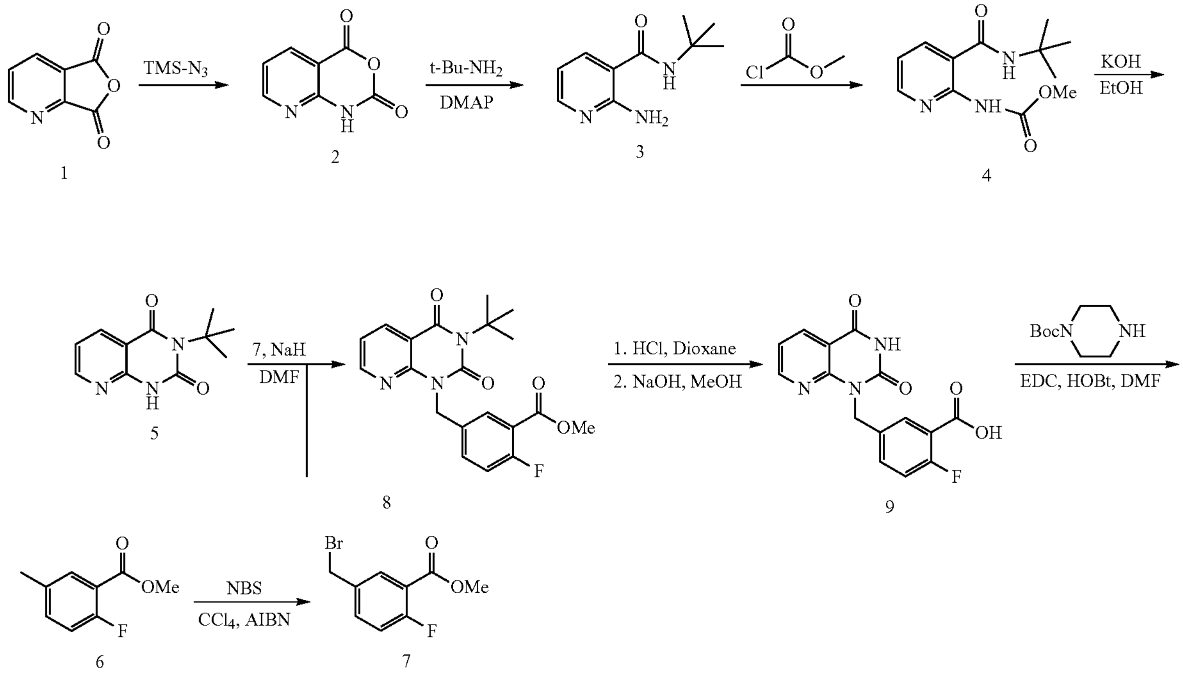

-continued

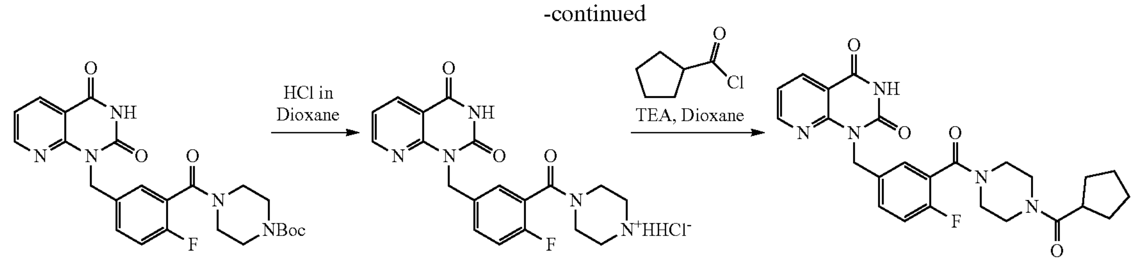

10 11 TRA-13F

Example 1b: Synthesis of 1-(3-(4-(cyclopentanecarbonyl) piperazine-1-carbonyl)-4-fluorobenzyl) pyrido[2,3-d]pyrimidine-2,4(1H,3H)-dione (TRA-13F)

Scheme-1

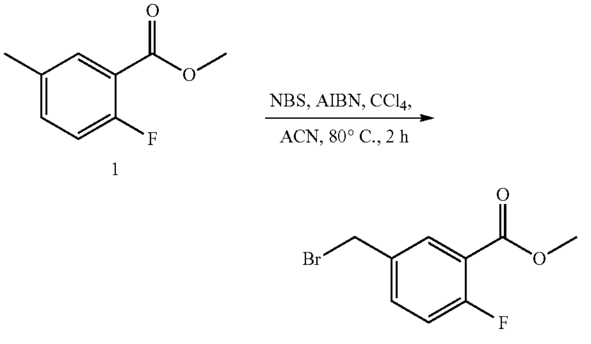

1

2

Synthesis of methyl 5-(bromomethyl)-2-fluorobenzoate (2): Methyl 2-fluoro-5-methylbenzoate (8, 6.70 g, 40.0 mmol) was stirred in carbon tetra chloride:acetonitrile (120.0 mL, 5:1) and N-bromosuccinamide (7.47 g, 42.0 mmol) was added followed by addition of and AIBN (1.29 g, 8.0 mmol). The resulting mixture and heated at 80° C. for 2 h. After consumption of starting material (monitored by TLC), the reaction mixture was diluted with water (25 mL) and extracted with dichloromethane (3×100 mL). The combined organic layer was washed with ice water (50 mL) and brine (50 mL), dried over anhydrous sodium sulfate and evaporated under reduced pressure to give crude methyl 5-(bromomethyl)-2-fluorobenzoate (2, 6.0 g, 61%) as a white solid.

$^1H$ NMR (400 MHz, DMSO-$d_6$): δ 7.98-8.02 (m, 1H), 7.73-7.80 (m, 1H), 7.31-7.40 (m, 1H), 4.78 (s, 2H), 3.87 (s, 3H).

Scheme-2

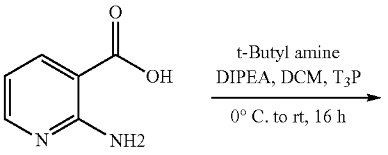

3

-continued

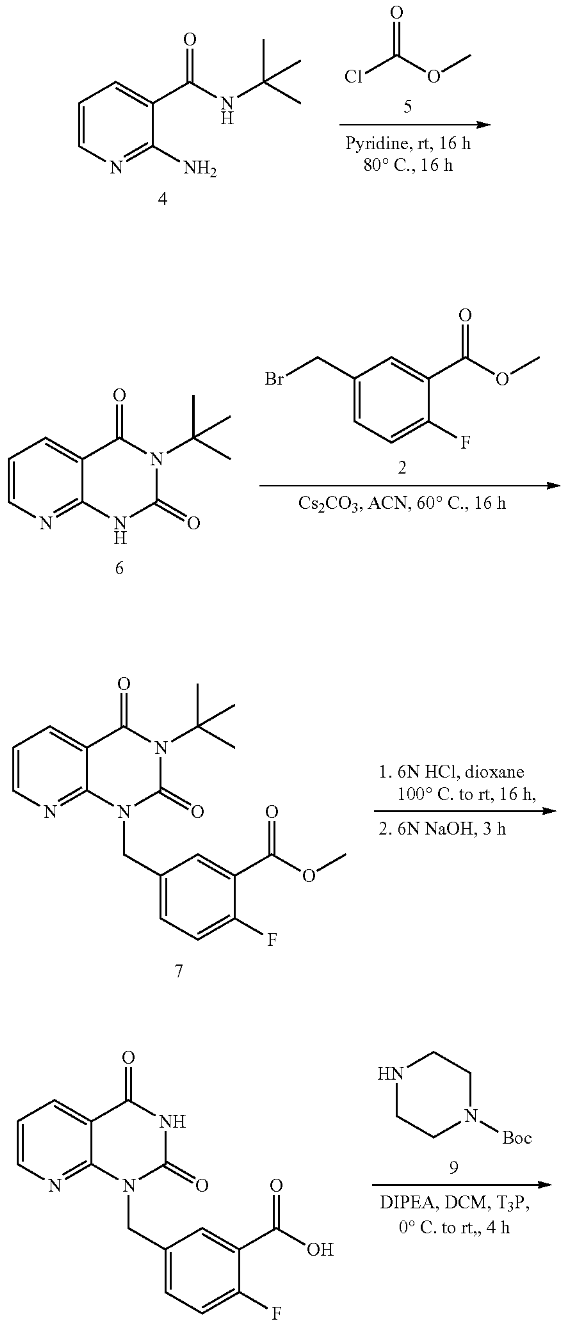

4 5 6 2 7 8 9

-continued

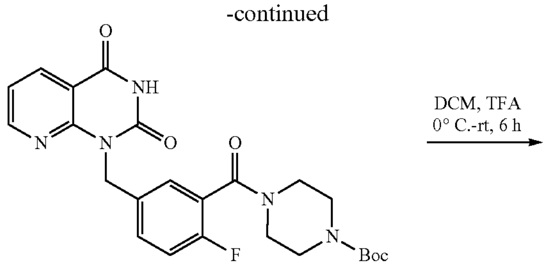

10

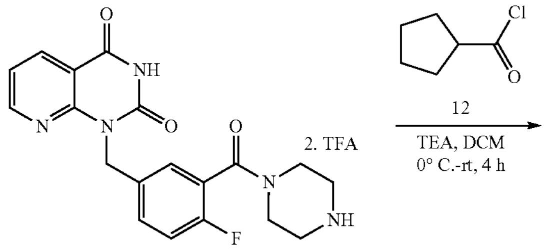

11

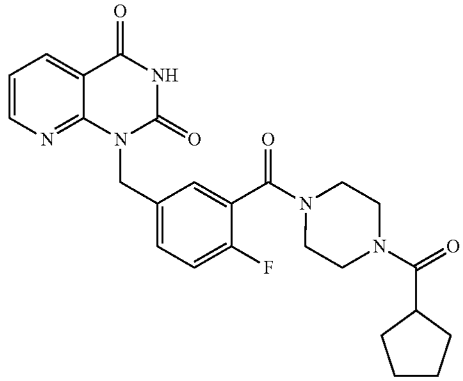

TRA-13F

Synthesis of 2-amino-N-(tert-butyl)nicotinamide (4): To a solution of 2-aminonicotinic acid (1, 10.0 g, 72.46 mmol), tert-butyl amine (2, 15.28 g, 144.9 mmol) and DIPEA (38.0 mL, 218.80 mmol) in DCM (200 mL) and $T_3P$ (50% solution in EtOAc, 92.0 mL, 144.9 mmol) was added at 0° C. the reaction mixture was stirred at room temperature for 16 h. After consumption of starting material (monitored by TLC), the reaction mixture was diluted with water (100 mL) and extracted with dichloromethane (3×100 mL). The combined organic layer was washed with brine (100 mL), dried over anhydrous sodium sulfate and evaporated under reduced pressure to give crude 2-amino-N-(tert-butyl) nicotinamide (4, 5.60 g, 40%) as a white solid.

$^1$H-NMR (400 MHz; DMSO-d6): δ 6.50-6.55 (m, 1H), 6.83 (bs, 2H), 7.71 (bs, 1H), 7.77-7.82 (m, 1H), 8.00-8.05 (m, 1H). LCMS: m/z 194.10 $[M+H]^+$, 95.11%.

Synthesis of 3-(tert-butyl)pyrido[2,3-d]pyrimidine-2,4(1H,3H)-dione (6): To a solution of 2-amino-N-(tert-butyl) nicotinamide (4, 5.0 g, 25.9 mmol) in pyridine (10.0 mL) and methyl chloroformate (4, 5.0 mL, 42.5 mmol) was added dropwise at 0° C. The reaction mixture was stirred at room temperature for 16 h, which was further continued at 80° C. for 16 h. After consumption of starting material (monitored by TLC), the reaction mixture was diluted with water and solid was precipitated which was filtered and dried under reduced pressure to give 3-(tert-butyl)pyrido[2,3-d]pyrimidine-2,4(1H,3H)-dione (6, 1.95 g, 34%) as a white solid.

LCMS: m/z 218.12 $[M-H]^+$, 90%.

Synthesis of methyl 5-((3-(tert-butyl)-2,4-dioxo-3,4-dihydropyrido[2,3-d]pyrimidin-1(2H)-yl)methyl)-2-fluorobenzoate (7): To a solution of 3-(tert-butyl)pyrido[2,3-d]pyrimidine-2,4(1H,3H)-dione (6, 1.5 g, 6.84 mmol), methyl 5-(bromomethyl)-2-fluorobenzoate (2, 1.68 g, 6.84 mmol) in ACN (30 mL) and $Cs_2CO_3$ (4.46 mL, 13.68 mmol) was added to it. The reaction mixture was stirred at 60° C. for 16 h. After consumption of starting material (monitored by TLC), the reaction mixture was diluted with water (50 mL) and extracted with EtOAc (3×50 mL). The combined organic layer was washed with brine (50 mL), dried over anhydrous sodium sulfate and evaporated under reduced pressure to give crude compound which was purified by flash column chromatography [normal phase, silica gel (100-200 mesh), gradient 20% to 25% ethyl acetate in hexane] to give methyl 5-((3-(tert-butyl)-2,4-dioxo-3,4-dihydropyrido[2,3-d]pyrimidin-1(2H)-yl)methyl)-2-fluorobenzoate (7, 1.90 g, 30%) as a white solid.

LCMS: m/z 386.07 $[M+H]^+$, 85%.

Synthesis of 5-((2,4-dioxo-3,4-dihydropyrido[2,3-d]pyrimidin-1(2H)-yl)methyl)-2-fluorobenzoic acid (8): Methyl 5-((3-(tert-butyl)-2,4-dioxo-3,4-dihydropyrido[2,3-d]pyrimidin-1(2H)-yl)methyl)-2-fluorobenzoate (7, 0.65 g, 1.68 mmol) was stirred in 1,4-dioxane (6.5 mL) and 6N HCl (6.5 mL). The reaction mass was heated at 100° C. for 16 h. After consumption of starting material (monitored by TLC), the reaction mixture was basified with 6N NaOH and stirred at room temperature for further 3 h. After completion, the reaction mixture was acidified with 10% sodium bisulfate solution, solid suspension was precipitated which was filtered and dried under reduced pressure to give 5-((2,4-dioxo-3,4-dihydropyrido[2,3-d]pyrimidin-1(2H)-yl)methyl)-2-fluorobenzoic acid (8, 0.55 g, 98%) as an off-white solid.

$^1$H-NMR (400 MHz; DMSO-d6): δ 5.37 (s, 2H), 7.20-7.28 (m, 1H), 7.30-7.35 (m, 1H), 7.55-7.62 (m, 1H), 7.85 (d, J=6 Hz, 1H), 8.36 (d, J=7.2 Hz, 1H), 8.69 (d, J=3.6 Hz, 1H), 11.85 (bs, 1H). LCMS: m/z 316.12 $[M+H]^+$, 95%;

Synthesis of tert-butyl 4-(5-((2,4-dioxo-3,4-dihydropyrido[2,3-d]pyrimidin-1(2H)-yl)methyl)-2-fluorobenzoyl)piperazine-1-carboxylate (10): To a solution of 5-((2,4-dioxo-3,4-dihydropyrido[2,3-d]pyrimidin-1(2H)-yl)methyl)-2-fluorobenzoic acid (8, 0.50 g, 1.42 mmol), tert-butyl piperazine-1-carboxylate (9, 0.319 mmol) and DIPEA (0.71 mL, 4.23 mmol) in dichloromethane (10.0 mL) and $T_3P$ (1.50 mL, 2.37 mmol, 50% solution in EtOAc) was added at 0° C. The reaction mixture and stirred at room temperature for 4 h. After consumption of starting material (monitored by TLC), the reaction mixture was diluted with water (25 mL) and extracted with dichloromethane (2×50 mL). The combined organic layer was washed with ice water (20 mL) and brine (20 mL), dried over anhydrous sodium sulfate and evaporated under reduced pressure to give crude tert-butyl 4-(5-((2,4-dioxo-3,4-dihydropyrido[2,3-d]pyrimidin-1(2H)-yl)methyl)-2-fluorobenzoyl)piperazine-1-carboxylate (10, 0.8 g, 94%) as a brown sticky solid.

$^1$H-NMR (400 MHz; DMSO-d6): δ 1.40 (s, 9H), 3.00-3.15 (m, 4H), 3.30-3.40 (m, 4H), 5.37 (s, 2H), 7.18-7.23 (m, 1H), 7.30-7.39 (m, 2H), 7.40-7.48 (m, 1H), 8.35-8.40 (m, 1H), 8.65-8.72 (m, 1H), 11.89 (bs, 1H). LCMS: m/z 484.26 $[M+H]^+$, 75%.

Synthesis of 1-(4-fluoro-3-(piperazine-1-carbonyl)benzyl)pyrido[2,3-d]pyrimidine-2,4(1H,3H)-dione. 2TFA (11): To a stirred solution of tert-butyl 4-(5-((2,4-dioxo-3,4-dihydropyrido[2,3-d]pyrimidin-1(2H)-yl)methyl)-2-fluorobenzoyl)piperazine-1-carboxylate (10, 0.80 g, 1.48 mmol) in dichloromethane (6.0 mL) was added trifluoroacetic acid (2.0 mL) at 0° C. and stirred at room temperature for 6 h. After consumption of starting material (monitored by TLC), the reaction mixture was evaporated under reduced pressure to give crude 1-(4-fluoro-3-(piperazine-1-carbonyl) benzyl) pyrido[2,3-d]pyrimidine-2,4(1H,3H)-dione. 2TFA (11, 1.0 g, crude) product as a sticky brown solid which was used for further step without purification.

$^{1}$H-NMR (400 MHz; DMSO-d6): δ 3.00-3.20 (m, 4H), 3.50-3.80 (m, 4H), 5.37 (s, 2H), 7.18-7.22 (m, 1H), 7.23-7.30 (m, 1H), 7.40-7.48 (m, 2H), 8.30-8.40 (m, 1H), 8.61-8.70 (m, 1H), 9.12 (bs, 2H), 10.00 (bs, 1H), 11.86 (bs, 1H). MS-ESI: m/z 384.27

Synthesis of 1-(3-(4-(cyclopentanecarbonyl)piperazine-1-carbonyl)-4-fluorobenzyl) pyrido [2,3-d]pyrimidine-2,4(1H, 3H)-dione (TRA-13F): To a solution of 1-(4-fluoro-3-(piperazine-1-carbonyl)benzyl)pyrido[2,3-d]pyrimidine-2,4 (1H,3H)-dione. 2TFA (11, 0.60 g, 0.73 mmol; calculated considering 75% LCMS purity), TEA (0.68 mL, 4.90 mmol) in dichloromethane (10.0 mL) and cyclopentane carbonyl chloride (12, 0.19 g, 1.47 mmol) was added at 0° C. The reaction mixture was stirred at room temperature for 4 h. After consumption of starting material (monitored by TLC), the reaction mixture was diluted with water (25 mL) and extracted with dichloromethane (3×30 mL). The combined organic layer was washed brine (20 mL), dried over anhydrous sodium sulfate and evaporated under reduced pressure to give crude residue. The residue was purified by prep-HPLC (Reverse phase, Sunfire (19×250) mm, 10μ, gradient 17%:52% ACN in 12 min containing 5 mM AA, RT: 11.27 min) to give 1-(3-(4-(cyclopentanecarbonyl)piperazine-1-carbonyl)-4-fluorobenzyl)pyrido[2,3-d]pyrimidine-2,4(1H, 3H)-dione (TRA-13F, 140 mg, 40%) as a white solid.

$^{1}$H NMR (400 MHz, DMSO-$d_6$): δ 1.45-1.80 (m, 9H), 2.88-3.02 (m, 1H), 3.10-3.20 (m, 2H), 3.30-3.40 (m, 2H), 3.50-3.65 (m, 4H), 5.37 (s, 2H), 7.21 (t, J=9.2 Hz, 1H), 7.30-7.35 (m, 1H), 7.39 (d, J=5.3 Hz, 1H), 7.42-7.48 (m, 1H), 8.36 (d, J=7.7 Hz, 1H), 8.67 (d, J=3.6 Hz, 1H), 11.82 (bs, 1H). LCMS: m/z 478.10 $[M+H]^+$, 97.74%.

Example 2a: TRA-13F-FL Synthesis

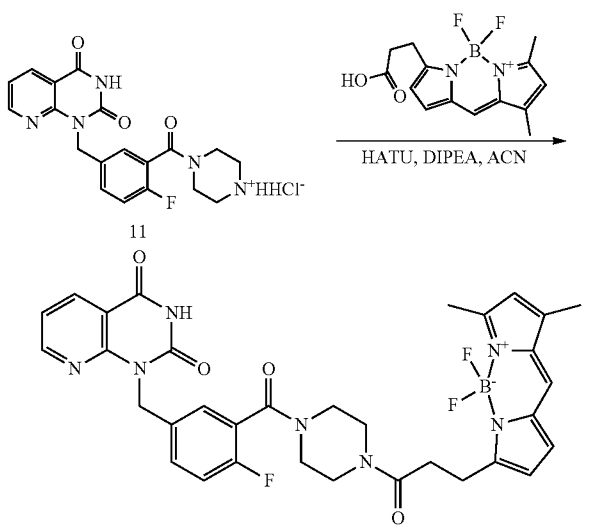

11

TRA-13F-FL

Example-2b: Synthesis of 1-(3-(4-(3-(5,5-difluoro-7,9-dimethyl-5H-5I4,6I4-dipyrrolo[1,2-c:2',1'-f][1,3,2]diazaborinin-3-yl)propanoyl) piperazine-1-carbonyl)-4-fluorobenzyl)pyrido[2,3-d]pyrimidine-2,4 (1H,3H)-dione (TRA-13F-FL)

Scheme-3

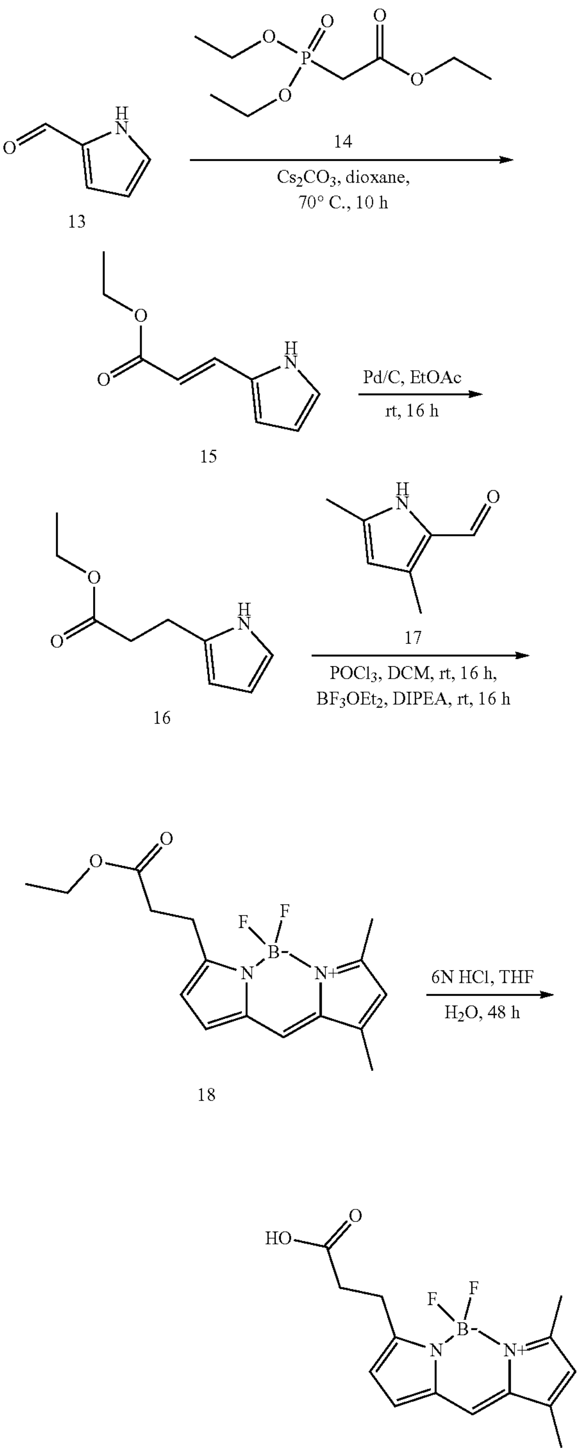

13 14 15 16 17 18 19

-continued

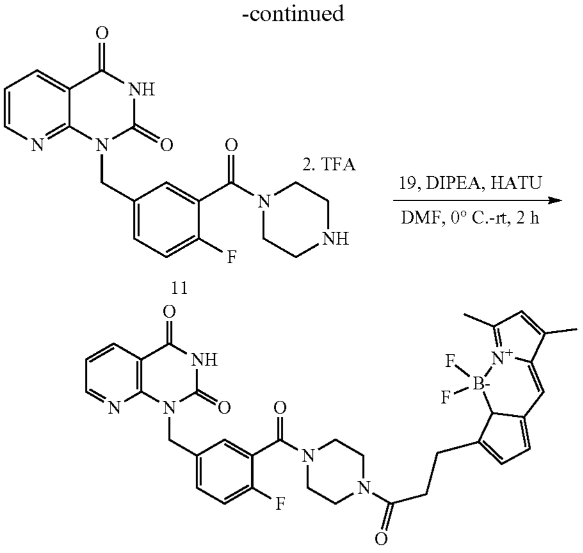

11

TRA-13F-FL

Synthesis of ethyl (E)-3-(1H-pyrrol-2-yl)acrylate (15): Ethyl 2-(diethoxyphosphoryl)acetate (13, 1.0 g, 10.52 mmol), $Cs_2CO_3$ (5.1 g, 15.70 mmol) was stirred in 1,4-dioxane (10.0 mL) and water (0.1 mL) for 30 min and 1H-pyrrole-2-carbaldehyde (14, 2.80 g, 12.62 mmol) was added to it. The reaction mixture was stirred at 70° C. for 10 h. After consumption of starting material, the reaction mixture was diluted with water (25 mL) and extracted with EtOAc (3×50 mL). The combined organic layer was washed with ice water and brine, dried over anhydrous sodium sulfate and evaporated under reduced pressure to give ethyl (E)-3-(1H-pyrrol-2-yl)acrylate (15, 1.3 g, 76%) as a brown color Liquid.

$^1$H NMR (400 MHz, DMSO-$d_6$): δ 1.22 (t, J=6.8 Hz, 3H), 3.56 (s, 2H), 4.13 (q, J=7.2 Hz, 2H), 6.13-6.21 (m, 2H), 6.56 (s, 1H), 7.02 (s, 1H), 7.40-7.48 (m, 1H). LCMS: m/z 166.10 $[M+H]^+$, 96%.

Synthesis of ethyl ethyl 3-(1H-pyrrol-2-yl) propanoate (16): To a solution of ethyl (E)-3-(1H-pyrrol-2-yl) acrylate (15, 1.3 g, 7.87 mmol) in EtOAc (50.0 mL) and 10% Pd on charcoal (0.3 g, 50% wet) was added. The reaction mixture was stirred at room temperature for 16 h under $H_2$ atmosphere. After consumption of starting material (monitored by TLC), the reaction mixture was filtered through a pad of celite, washed with MeOH and concentrated in vacuo. The residue was purified by flash column chromatography [normal phase, silica gel (100-200 mesh), gradient 10% to 15% ethyl acetate in hexane] to give ethyl 3-(1H-pyrrol-2-yl) propanoate (16, 1.25 g, 96%) as a colorless liquid.

$^1$H NMR (400 MHz, DMSO-$d_6$): δ1.10-1.20 (m, 3H), 2.50-2.60 (m, 2H), 2.70-2.80 (m, 2H), 4.00-4.10 (m, 2H), 5.71 (s, 1H), 5.86 (d, J=2.5 Hz, 1H), 6.56 (s, 1H), 10.57 (bs, 1H). LCMS: m/z 168.15 $(M+H)^+$, 84%.

Synthesis of ethyl 3-(5,5-difluoro-7,9-dimethyl-5H-5I4,6I4-dipyrrolo[1,2-c:2',1'-f][1,3,2]diazaborinin-3-yl)propanoate (18): Ethyl 3-(1H-pyrrol-2-yl)propanoate (16, 1.2 g, 7.18 mmol) and 3,5-dimethyl-1H-pyrrole-2-carbaldehyde (17, 0.90 g, 7.31 mmol) was stirred in dry DCM (48.0 mL) and POCl3 (0.75 mL, 8.04 mmol) was added to it. The reaction mixture was stirred at room temperature for 16 h then Boron trifluoride etherate (3.58 mL, 29.24 mmol) and DIPEA (5.30 mL, 30.70 mmol) were added at room temperature. The resulting mixture was stirred for 16 h at room temperature. After consumption of starting material (monitored by TLC), the reaction mixture was diluted with water (25 mL) and extracted with DCM (3×50.0 mL). The combined organic layer was washed with brine (30 mL), dried over anhydrous sodium sulfate and evaporated under reduced pressure to give the residue. The residue was purified by flash column chromatography [normal phase, silica gel (100-200 mesh), gradient 20% to 25% ethyl acetate in hexane] to ethyl 3-(5,5-difluoro-7,9-dimethyl-5H-5I4,6I4-dipyrrolo[1,2-c:2',1'-f][1,3,2]diazaborinin-3-yl)propanoate (18, 1.25 g, 54%) as a brown solid. 1H NMR (400 MHz, DMSO-d6): δ 1.18 (t, J=6.8 Hz, 3H), 2.26 (s, 3H), 2.42 (s, 3H), 2.70-2.74 (m, 2H), 3.08-3.12 (m, 2H), 4.07 (q, J=7.2 Hz, 2H), 6.31 (s, 1H), 6.36 (d, J=4.0 Hz, 1H), 7.08 (d, J=3.6 Hz, 1H), 7.71 (s, 1H). LCMS: m/z 319.21 (M+H)+, 99%

Synthesis of 3-(5,5-difluoro-7,9-dimethyl-5H-5I4,6I4-dipyrrolo[1,2-c:2',1'-f][1,3,2]diaza borinin-3-yl)propanoic acid (19): To a solution of ethyl 3-(5,5-difluoro-7,9-dimethyl-5H-5I4,6I4-dipyrrolo[1,2-c:2',1'-f][1,3,2]diazaborinin-3-yl)propanoate (18, 1.25 g, 3.90 mmol) in THE (187.5 mL), conc HCl (62.5 mL) and water (125.0 mL) were added in the reaction mixture. The resulting mixture was stirred at room temperature for 48 h. After consumption of starting material (monitored by TLC), the compound was extracted with DCM (125.0 mL). The combined organic layer was washed with brine, dried over anhydrous sodium sulfate and evaporated under reduced pressure to give crude 3-(5,5-difluoro-7,9-dimethyl-5H-5I4,6I4-dipyrrolo[1,2-c:2',1'-f][1,3,2]diazaborinin-3-yl)propanoic acid (19, 1.15 g, crude) as a brown solid.

LCMS: m/z 291.14 $(M-H)^+$, 80%

Synthesis of 1-(3-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-4-fluorobenzyl)pyrido[2,3-d]pyrimidine-2,4(1H,3H)-dione (TRA-13F-FL): To a solution of 1-(4-fluoro-3-(piperazine-1-carbonyl)benzyl) pyrido[2,3-d]pyrimidine-2,4(1H,3H)-dione. 2TFA (11, 0.3 g, 0.51 mmol, calculated considering 75% LCMS purity) and 3-(5,5-difluoro-7,9-dimethyl-5H-5I4,6I4-dipyrrolo[1,2-c:2',1'-f][1,3,2]diazaborinin-3-yl)propanoic acid (19, 0.16 g, 0.438 mmol, calculated considering 80% of starting material) in DMF (8.0 mL), DIPEA (0.34 mL, 1.96 mmol) and HATU (0.37 g, 0.95 mmol) were added to it at 0° C. The reaction mixture was stirred at room temperature for 2 h. After consumption of starting material (monitored by TLC), the reaction mixture was diluted with ice water and solid was filtered. The solid residue was dried under reduced pressure to give crude residue which was purified by prep-HPLC (Reverse phase, X Select Phenyl Hexyl (19×250) mm, 10μ, gradient 30%: to 65% ACN in 11 min containing 0.1% TFA, RT: 10.5 min) to give 1-(3-(4-(3-(5,5-difluoro-7,9-dimethyl-5H-5I4,6I4-dipyrrolo[1,2-c:2',1'-f][1,3,2]diazaborinin-3-yl) propanoyl)piperazine-1-carbonyl)-4-fluorobenzyl)pyrido[2,3-d]pyrimidine-2,4(1H,3H)-dione (TRA-13F-FL, 0.14 g, 41%) as a reddish brown solid.

$^1$H NMR (400 MHz, DMSO-$d_6$): δ 2.26 (s, 3H), 2.46 (s, 3H), 2.66-2.71 (m, 1H), 2.75-2.79 (m, 1H), 3.02-3.10 (m, 2H), 3.11-3.20 (m, 2H), 3.32-3.42 (m, 2H), 3.50-3.62 (m, 4H), 5.37 (s, 2H), 6.29 (s, 1H), 6.37 (dd, J=14.2, 3.8 Hz, 1H), 7.09 (s, 1H), 7.25 (t, J=9.0 Hz, 1H), 7.35-7.29 (m, 1H), 7.40 (d, J=6.2 Hz, 1H), 7.46 (bs, 1H), 7.69 (s, 1H), 8.37 (d, J=7.6 Hz, 1H), 8.67 (s, 1H), 11.84 (s, 1H). LCMS: m/z 658.28 $[M+H]^+$ $(ES^+)$, 98.93%.

Synthesis of Compounds of Formula III

Example 3a: TRA-14F Synthesis

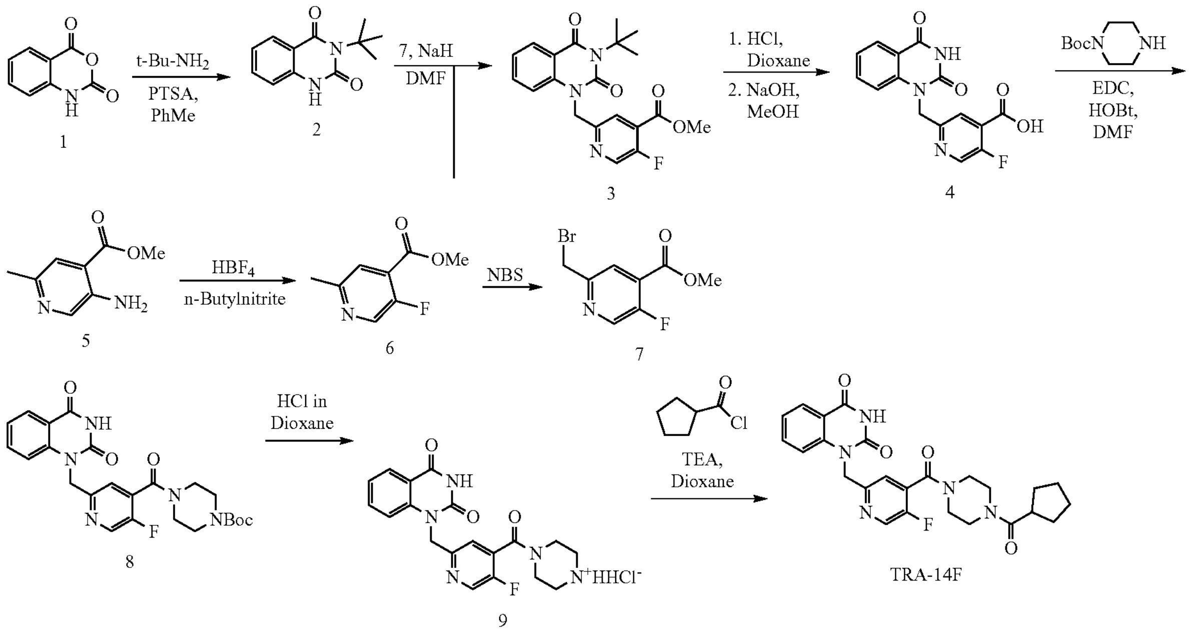

Example-3b

Synthesis of 1-((4-(4-(cyclopentanecarbonyl)piperazine-1-carbonyl)-5-fluoropyridin-2-yl)methyl)quinazoline-2,4(1H,3H)-dione (TRA-14F)

Scheme-4

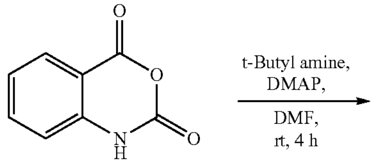

20

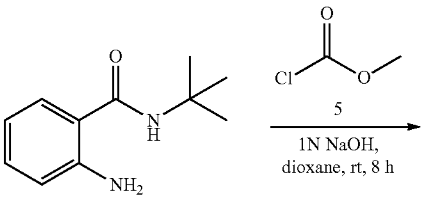

21

-continued

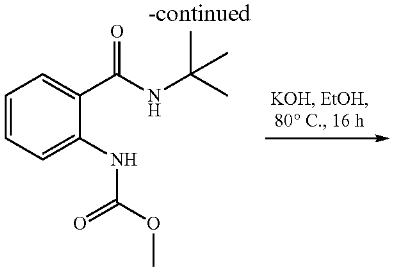

22

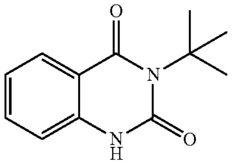

23

Synthesis of 2-amino-N-(tert-butyl)benzamide (21): To a solution of 2H-benzo[d][1,3]oxazine-2,4(1H)-dione (12, 12.0 g, 73.60 mmol) and tert-butyl amine (8.53 mL, 80.96 mmol) in DMF (75.0 mL), DMAP (1.35 g, 11.04 mmol) was added in the reaction mixture and stirred at room temperature for 5 h. After completion of reaction (monitored by TLC), the reaction mixture was diluted with water and solid was filtered and dried under reduced pressure to get 2-amino-N-(tert-butyl)benzamide (21, 9.0 g, 63%) as a white solid.

LCMS: m/z 191.13 $[M+H]^+$, 92%

Synthesis of methyl (2-(tert-butylcarbamoyl)phenyl)carbamate (22): To a solution of 2-amino-N-(tert-butyl)benzamide (21, 5.46 g, 2.82 mmol) and methylchloroformate (5, 2.65 g, 2.82 mmol) in 1,4-dioxane (44.0 mL) and 1N NaOH solution (32.0 mL) was added in the reaction mixture. The reaction mass was stirred at room temperature for 3 h. After consumption of starting material, the reaction mixture was diluted with water (80 mL) and extracted with ethyl acetate (2×50 mL). The combined organic layer was washed with brine (20 mL), dried over anhydrous sodium sulfate and evaporated under reduced pressure to give crude methyl (2-(tert-butylcarbamoyl)phenyl)carbamate (22, 5.5 g, crude) as a brown solid.

$^1$H NMR (400 MHz, DMSO-$d_6$): δ 1.37 (s, 9H), 3.67 (s, 3H), 7.01 (t, J=7.6 Hz, 1H), 7.46 (t, J=7.2 Hz, 1H), 7.65 (d, J=8 Hz, 1H), 8.04 (bs, 1H), 8.09 (d, J=8.4 Hz, 1H), 10.56 (bs, 1H).

LCMS: m/z 251.17 [M+H]$^+$, 99%

Synthesis of 3-(tert-butyl)quinazoline-2,4(1H,3H)-dione (23): To a solution of methyl (2-(tert-butylcarbamoyl)phenyl)carbamate (22, 5.0 g, 15.82 mmol) in EtOH (100.0 mL) and powder KOH (10.0 g) was added in the reaction mixture. The resulting mixture was stirred at 80° C. for 16 h. After consumption of starting material, the reaction mixture was diluted with water and solid was filtered and dried under reduced pressure to give 3-(tert-butyl)quinazoline-2,4(1H,3H)-dione (23, 2.5 g, 72%) as a white solid.

$^1$H NMR (400 MHz, DMSO-$d_6$): δ 1.66 (s, 9H), 7.02-7.18 (m, 2H), 7.57 (t, J=7.2 Hz, 1H), 7.82 (d, J=8 Hz, 1H), 11.71 (bs, 1H). LCMS: m/z 219.16 [M+H]$^+$, 99.75%

Scheme 5

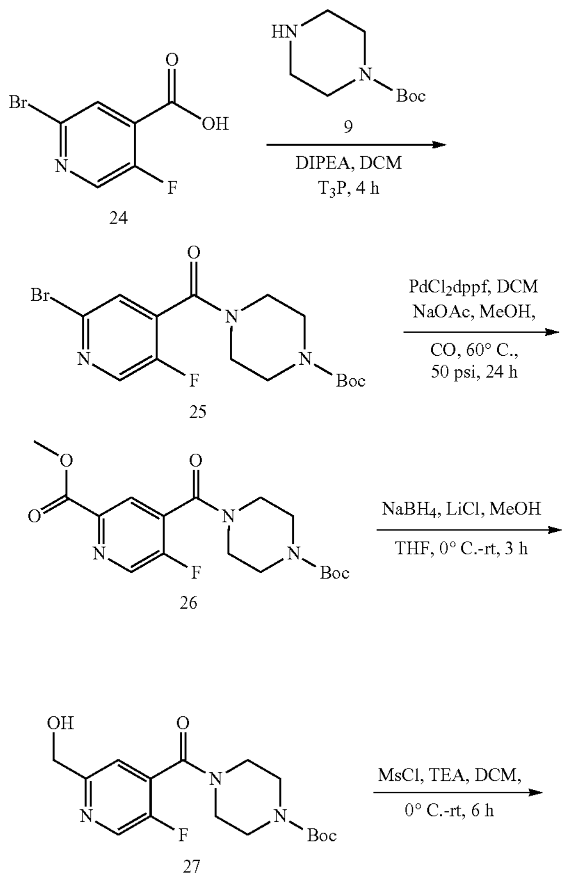

-continued

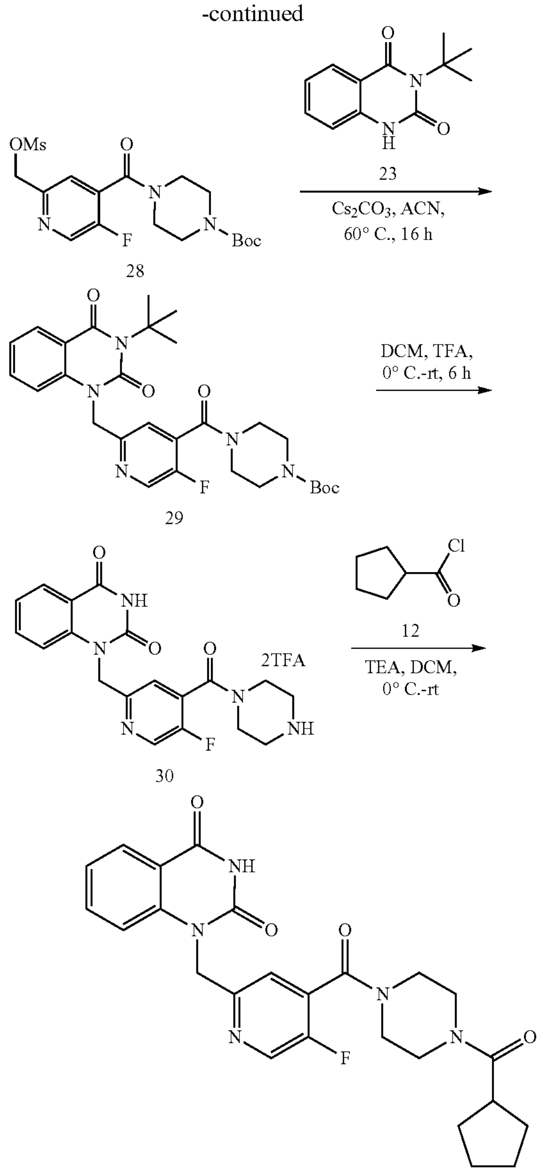

TRA-14F

Synthesis of tert-butyl 4-(2-bromo-5-fluoroisonicotinoyl) piperazine-1-carboxylate (25): To a solution of 2-bromo-5-fluoroisonicotinic acid (24, 5.0 g, 22.72 mmol), and tert-butyl piperazine-1-carboxylate (9, 5.0 g, 27.27 mmol) in DCM (100.0 mL), DIPEA (11.8 mL, 68.16 mmol) and $T_3P$ (21.6 mL, 34.08 mmol, 50% solution in EtOAc) were added at 0° C. The reaction mixture and stirred at room temperature for 4 h. After consumption of starting material (monitored by TLC), the reaction mixture was diluted with water (100 ml) and extracted with dichloromethane (3×100 mL). The combined organic layer was washed with brine (50 mL), dried over anhydrous sodium sulfate and evaporated under reduced pressure to give tert-butyl 4-(2-bromo-5-fluoroisonicotinoyl) piperazine-1-carboxylate (25, 8.0 g, 91%) as an off white solid.

$^1$H-NMR (400 MHz; DMSO-d6): 1.40 (s, 9H), 3.22-3.30 (m, 4H), 3.40-3.42 (m, 2H), 3.58-3.63 (m, 2H), 8.83 (d, J=5.2 Hz, 1H), 8.64 (s, 1H). LCMS: m/z 388.05 [M+H]$^+$, 99%

Synthesis of tert-butyl 4-(5-fluoro-2-(methoxycarbonyl) isonicotinoyl)piperazine-1-carboxylate (26): To a solution of tert-butyl 4-(2-bromo-5-fluoroisonicotinoyl)piperazine-1-carboxylate (25, 4.0 g, 10.33 mmol) in MeOH (120.0 mL), NaOAc (1.27 g, 15.49 mmol) and $PdCl_2$(dppf). DCM (0.84 g, 1.03 mmol) were added in the reaction mixture which was purged with argon for 15 min and stirred at 60° C. for 24 h in pressure vessel at 60 psi under CO atmosphere. After consumption of starting material, the reaction mixture was cooled to room temperature and then the reaction mass was filtered through a pad of celite, thoroughly washed with MeOH and concentrated under reduced pressure. The residue was purified by flash column chromatography [normal phase, silica gel (100-200 mesh), gradient 25% to 30% ethyl acetate in hexane] to give tert-butyl 4-(5-fluoro-2-(methoxycarbonyl)isonicotinoyl)piperazine-1-carboxylate (4, 2.50 g, 66%) as a white solid.

$^1$H-NMR (400 MHz; DMSO-d6): 1.40 (s, 9H), 3.20-3.23 (m, 2H), 3.30-3.33 (m, 2H), 3.40-3.45 (m, 2H), 3.60-3.65 (m, 2H), 3.89 (s, 3H), 8.17 (d, J=5.2 Hz, 1H), 8.82 (s, 1H). LCMS: m/z 368.23 $[M+H]^+$, 93%

Synthesis of tert-butyl 4-(5-fluoro-2-(hydroxymethyl) isonicotinoyl)piperazine-1-carboxylate (27): To a solution of tert-butyl 4-(5-fluoro-2-(methoxycarbonyl)isonicotinoyl) piperazine-1-carboxylate (26, 2.5 g, 6.79 mmol) in MeOH: THF (50 mL, 1:1), lithium chloride (0.29 g, 6.79 mmol) and sodium borohydride (0.50 g, 13.58 mmol) were added portion wise at 0° C. The reaction mixture was stirred at room temperature for 3 h. After consumption of starting material (monitored by TLC), reaction was quenched with water (30.0 mL) and concentrated under reduced pressure. The residue was diluted with water (50.0 mL) and extracted with ethyl acetate (2×50 mL). The combined organic layer was washed with brine (20 mL), dried over anhydrous sodium sulfate and evaporated under reduced pressure to give crude tert-butyl 4-(5-fluoro-2-(hydroxymethyl)isonicotinoyl)piperazine-1-carboxylate (27, 2.40 g, crude) as a brown solid.

LCMS: m/z 340.23 $[M+H]^+$, 70%

Synthesis of tert-butyl 4-(5-fluoro-2-(((methylsulfonyl) oxy)methyl)isonicotinoyl)piperazine-1-carboxylate (28): To a solution of tert-butyl 4-(5-fluoro-2-(hydroxymethyl)isonicotinoyl)piperazine-1-carboxylate (27, 1.68 g, 4.95 mmol, calculated considering 70% purity) in dichloromethane (48.0 mL), $Et_3N$ (2.95 mL, 21.23 mmol) and MsCl (1.64 g, 21.21 mmol) were sequentially added at 0° C. The reaction mixture was stirred at room temperature for 6 h. After consumption of starting material (monitored by TLC), the reaction mixture was diluted with water (50 mL) and extracted with DCM (3×50 mL). The combined organic layer was washed brine (20 mL), dried over anhydrous sodium sulfate and evaporated under reduced pressure to give crude tert-butyl 4-(5-fluoro-2-(((methylsulfonyl)oxy) methyl)isonicotinoyl)piperazine-1-carboxylate (28, 3.0 g, crude) as a brown solid which was used for the next step without purification.

Synthesis of tert-butyl 4-(2-((3-(tert-butyl)-2,4-dioxo-3,4-dihydroquinazolin-1(2H)-yl)methyl)-5-fluoroisonicotinoyl) piperazine-1-carboxylate (29): 3-(tert-butyl)quinazoline-2,4 (1H,3H)-dione (23, 1.20 g, 5.50 mmol), tert-butyl 4-(5-fluoro-2-(((methylsulfonyl)oxy) methyl)isonicotinoyl) piperazine-1-carboxylate (28, 2.76 g, 6.60 mmol) and $Cs_2CO_3$ (3.57 g, 11.0 mmol) was stirred in ACN (50.0 mL) at 60° C. for 16 h. After consumption of starting material (monitored by TLC), the reaction mixture was diluted with water (30 mL) and extracted with EtOAc (2×30 mL). The combined organic layer was washed with brine (20 mL), dried over anhydrous sodium sulfate and evaporated under reduced pressure to give crude. The crude was purified by flash column chromatography [normal phase, silica gel (100-200 mesh), gradient 30% to 40% ethyl acetate in hexane] to give tert-butyl 4-(2-((3-(tert-butyl)-2,4-dioxo-3,4-dihydroquinazolin-1(2H)-yl)methyl)-5-fluoroisonicotinoyl) piperazine-1-carboxylate (29, 1.20 g, 41%) as a white solid.

$^1$H-NMR (400 MHz; DMSO-d6): δ 1.44 (s, 9H), 3.18-3.21 (m, 2H), 3.20-3.23 (m, 2H), 3.38-3.41 (m, 2H), 3.58-3.62 (m, 2H), 5.37 (s, 2H), 7.26-7.20 (m, 2H), 7.49 (d, J=5.0 Hz, 1H), 7.59 (t, J=7.9 Hz, 1H), 7.93 (d, J=6.7 Hz, 1H), 8.60 (s, 1H). LCMS: m/z 540.22 $[M+H]^+$, 83%

Synthesis of 1-((5-fluoro-4-(piperazine-1-carbonyl)pyridin-2-yl)methyl)quinazoline-2,4(1H,3H)-dione. 2TFA (30): To a stirred solution of tert-butyl 4-(2-((3-(tert-butyl)-2,4-dioxo-3,4-dihydroquinazolin-1(2H)-yl)methyl)-5-fluoroisonicotinoyl)piperazine-1-carboxylate (29, 1.20 g, 2.22 mmol) in dichloromethane (24.0 mL), trifluoroacetic acid (12.0 mL) was added at 0° C. and reaction mass was stirred at room temperature for 6 h. After consumption of starting material (monitored by TLC), the reaction mixture was evaporated under reduced pressure to give crude 1-((5-fluoro-4-(piperazine-1-carbonyl)pyridin-2-yl)methyl)quinazoline-2,4(1H,3H)-dione. 2TFA (30, 1.20 g, crude) as an off-white solid.

$^1$H-NMR (400 MHz; DMSO-d6): δ 2.90-3.00 (m, 2H), 3.18-3.22 (m, 2H), 3.33-3.43 (m, 2H), 3.78-3.83 (m, 2H), 5.41 (s, 2H), 7.26-7.20 (m, 2H), 7.54 (d, J=5.0 Hz, 1H), 7.63 (t, J=7.9 Hz, 1H), 8.03 (d, J=8.4 Hz, 1H), 8.65 (s, 1H), 8.78 (bs, 1H), 11.74 (s, 1H). LCMS: m/z 384.01 $[M+H]^+$, 80%

Synthesis of 1-((4-(4-(cyclopentanecarbonyl)piperazine-1-carbonyl)-5-fluoropyridin-2-yl)methyl)quinazoline-2,4 (1H,3H)-dione (TRA-14F): To a solution of 1-((5-fluoro-4-(piperazine-1-carbonyl)pyridin-2-yl)methyl)quinazoline-2, 4(1H,3H)-dione. 2TFA (30, 0.50 g, 0.82 mmol) in DCM (10.0 mL), TEA (0.34 mL, 2.46 mmol) and cyclopentanecarbonyl chloride (12, 0.13 g, 0.98 mmol) were added at 0° C. The reaction mixture and stirred at room temperature for 4 h. After completion of reaction (monitored TLC), the reaction mixture was diluted with water (10.0 mL) and extracted with dichloromethane (3×50 mL). The combined organic layer was washed brine (20 mL), dried over anhydrous sodium sulfate and evaporated under reduced pressure to give crude residue. The crude was purified by flash column chromatography [normal phase, silica gel (100-200 mesh), gradient 2% to 4% MeOH in DCM] to give 1-((4-(4-(cyclopentanecarbonyl)piperazine-1-carbonyl)-5-fluoropyridin-2-yl)methyl) quinazoline-2,4 (1H,3H)-dione (TRA-14F, 140 mg, 36%) as a white solid.

$^1$H NMR (400 MHz, DMSO-$d_6$): δ 1.51-1.75 (m, 10H), 2.85-3.00 (m, 1H), 3.01-3.10 (m, 2H), 3.50-3.61 (m, 4H), 5.41 (s, 2H), 7.20-7.30 (m, 2H), 7.54 (t, J=5.0 Hz, 1H), 7.64 (t, J=7.9 Hz, 1H), 8.02 (d, J=7.7 Hz, 1H), 8.62 (d, J=3.1 Hz, 1H), 11.71 (s, 1H). LCMS: m/z 480.16 $[M+H]^+$ (ES+), 98.26%

Example 4a: TRA-14F-FL Synthesis

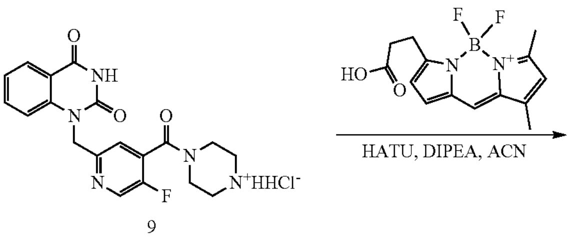

9

-continued

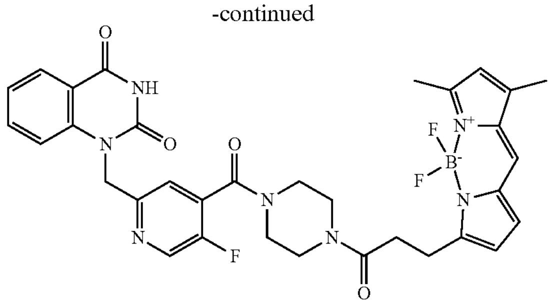

TRA-13F-FL

Example-4b Synthesis of 1-((4-(4-(3-(5,5-difluoro-7,9-dimethyl-5H-5I4,6I4-dipyrrolo[1,2-c:2',1'-f][1,3,2]diazaborinin-3-yl)propanoyl) piperazine-1-carbonyl)-5-fluoropyridin-2-yl)methyl)quinazoline-2,4(1H,3H)-dione (TRA-14F-FL)

Scheme-6

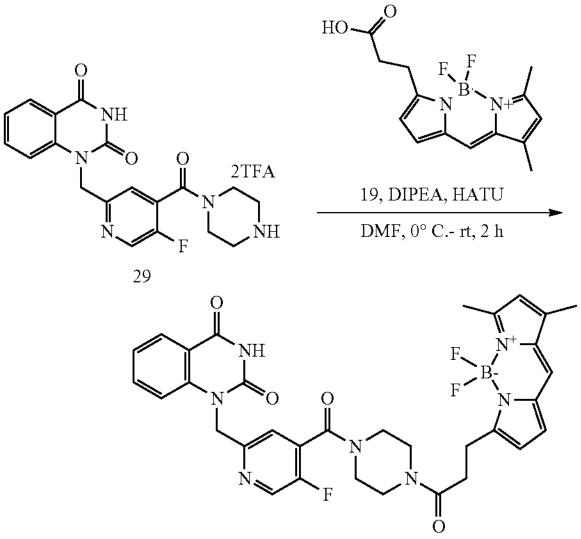

29

TRA-14F-FL

Synthesis of 1-((4-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-5-fluoropyridin-2-yl) methyl)quinazoline-2,4(1H,3H)-dione (TRA-14F-FL): To a solution of 1-((5-fluoro-4-(piperazine-1-carbonyl)pyridin-2-yl)methyl)quinazoline-2,4(1H,3H)-dione. 2TFA (29, 0.7 g, 1.14 mmol) and 3-(5,5-difluoro-7,9-dimethyl-5H-5I4,6I4-dipyrrolo[1,2-c:2',1'-f][1,3,2]diazaborinin-3-yl)propanoic acid (19, 0.27 g, 0.95 mmol; calculated considering 80% LCMS purity) in DMF (14.0 mL), DIPEA (0.60 mL, 3.44 mmol) and HATU (0.65 g, 1.72 mmol) were added at 0° C. The reaction mixture was stirred at room temperature for 2 h. After completion of reaction (monitored by TLC), the reaction mixture was diluted with ice water (40 mL) and solid was filtered to get residue. The obtained residue was dried under reduced pressure to give the crude material which was purified by flash column chromatography [normal phase, silica gel (100-200 mesh), gradient 2% to 5% MeOH in DCM] to give 1-((4-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-5-fluoropyridin-2-yl)methyl) quinazoline-2,4(1H,3H)-dione (TRA-14F-FL, 0.20 g, 27%) as a reddish brown solid.

$^1$H NMR (400 MHz, DMSO-$d_6$) δ: 2.26 (s, 3H), 2.46 (s, 3H), 2.62-2.80 (m, 1H), 2.78-2.75 (m, 2H), 3.01-3.10 (m, 2H), 3.11-3.20 (m, 2H), 3.30-3.40 (m, 2H), 3.51-3.63 (m, 4H), 5.41 (s, 2H), 6.30 (s, 1H), 6.43 (dd, J=12.6, 3.3 Hz, 1H), 7.09 (s, 1H), 7.20-7.28 (m, 2H), 7.54 (bs, 1H), 7.60-7.65 (m, 1H), 7.69 (s, 1H), 8.01 (d, J=7.4 Hz, 1H), 8.62 (s, 1H), 11.71 (s, 1H).

LCMS: m/z 658.31 $[M+H]^+$ (ES+), 96%.

Example-5

Synthesis of 1-(3-(4-(cyclopentanecarbonyl)piperazine-1-carbonyl)-4-iodo benzyl)pyrido[2,3-d]pyrimidine-2,4(1H,3H)-dione (TRA-131)

Scheme-7

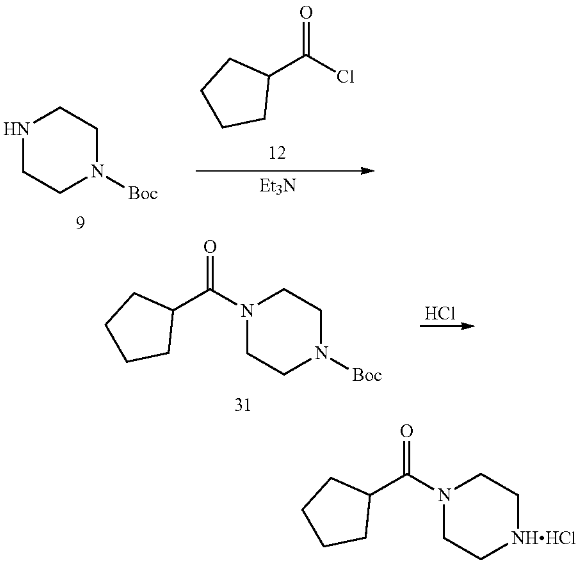

9

31

32

Synthesis of tert-butyl 4-(cyclopentanecarbonyl)piperazine-1-carboxylate (31)

To a solution of compound 9 (0.5 g, 2.6 mmol) and $Et_3N$ (1.1 mL, 8.0 mmol) in DCM (6 mL) was added compound 12 (0.35 g, 2.6 mmol) at 0° C. The mixture was stirred at RT for 2 hours. After completion, the suspension was dissolved in water and extracted with DCM. The organic layer was washed with brine solution, dried over $Na_2SO_4$ and concentrated under vacuo to afford compound 31 as a colorless gel. Yield: (0.75 g, 86%).

$^1$H-NMR (400 MHz; $CDCl_3$): δ 3.58 (s, 2H), 3.48 (s, 2H), 3.40-3.42 (m, 4H), 2.82-2.88 (m, 1H), 180-1.87 (m, 4H), 1.74-1.78 (m, 2H), 1.58-1.61 (m, 2H), 1.55 (s, 9H).

Synthesis of cyclopentyl(piperazin-1-yl)methanone hydrochloride (32)

To a solution of compound 31 (0.65 g, 2.3 mmol) in DCM (8 mL) was added 4N HCl in 1,4-dioxane (5 mL). The mixture was stirred for 1 h at RT. After completion, the solvents were removed under reduced pressure to give 32 as a white solid. Yield: (0.5 g, 90%).

$^1$H-NMR (400 MHz; DMSO-$d_6$): δ 9.37 (bs, 1H), 3.72 (m, 1H), 3.66 (m, 1H), 3.02-3.06 (m, 2H).

Scheme-8

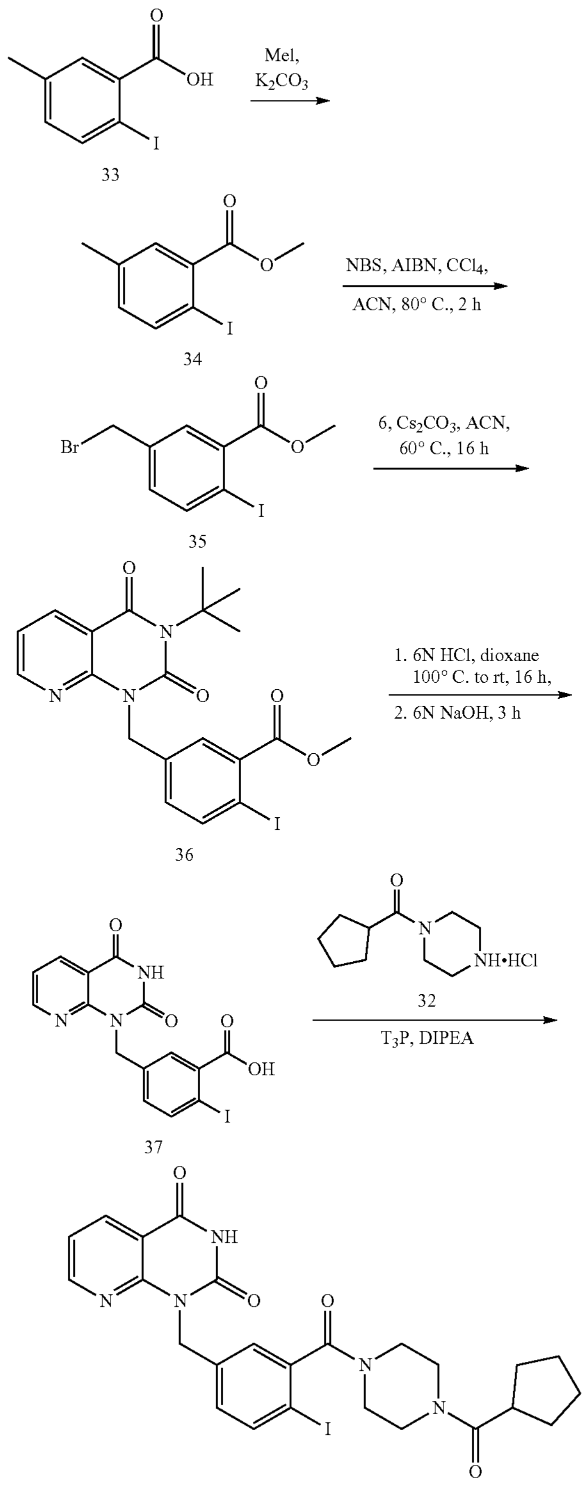

TRA-13I

Synthesis of methyl 2-iodo-5-methylbenzoate (34)

Compound 33 (16.0 g, 61.0 mmol) was dissolved in DMF (150 mL), then treated with potassium carbonate (16.9 g, 122 mmol) and MeI (6.3 mL, 95.7 mmol). The reaction mixture was stirred at RT for 16 h. After completion, the suspension was dissolved in water and extracted with EtOAc. The organic layer was washed with saturated NaCl solution, dried over $Na_2SO_4$ and concentrated in vacuo to afford a compound 34 as a brown liquid.

$^1$H-NMR (400 MHz; $CDCl_3$): δ 7.85 (s, 1H), 7.61 (s, 1H), 7.26 (s, 1H), 6.96-6.98 (d, 1H, J=6.8), 3.92 (s, 3H), 2.33 (s, 3H),

Yield: (15.2 g, 90%).

Synthesis of methyl 5-(bromomethyl)-2-iodobenzoate (35)

To a stirred solution of compound 34 (14.5 g, 52.0 mmol) in carbon tetrachloride (150 mL) was added N-Bromo succinimide (11.5 g, 63.0 mmol) followed by catalytic amount of benzoyl peroxide (0.86 g, 5.2 mmol). The solution was refluxed for 24 h. The reaction mixture was filtered to remove succinimide byproduct and the filtrate was washed with brine, dried over anhydrous $Na_2SO_4$ and evaporated under reduced pressure. The crude was purified by column chromatography on silica gel (5-8% EtOAc in hexanes) to give 35 as a white solid.

$^1$H-NMR (400 MHz; DMSO-d6): δ 7.96-7.98 (d, 1H, J=8.0 Hz), 7.82-7.83 (d, 1H, J=2.2 Hz), 7.17-7.18 (d, 1H, J=2.2 Hz), 4.43 (s, 1H), 3.94 (s, 3H).

Yield: (9.2 g, 50%).

Synthesis of methyl 5-((3-(tert-butyl)-2,4-dioxo-3,4-dihydropyrido[2,3-d]pyrimidin-1(2H)-yl)methyl)-2-iodobenzoate (36)

A suspension of compound 6 (2.7 g, 12.3 mmol), compound 35 (12.3 mmol), $CS_2CO_3$ (24.6 mmol) and acetonitrile was stirred at 80° C. for 16 h. After completion, the RM was diluted with water and extracted with EtOAc. The organic layer was dried over anhydrous $Na_2SO_4$ and evaporated under reduced pressure. The crude was purified by column chromatography on silica gel (10-15% EtOAc in hexanes) to give compound 36 as a white solid.

$^1$H-NMR (400 MHz; $CDCl_3$): δ 8.55-8.56 (m, 1H), 8.31-8.34 (dd, 1H, J=4 Hz, 8 Hz), 7.90-7.92 (m, 1H), 7.24 (s, 1H), 7.12-7.16 (m, 1H), 5.44 (s, 2H), 3.90 (s, 3H), 1.73 (s, 9H).

Yield: (3.6 g, 68%).

ESI-MS: m/z 494 $[M+1]^+$.

Synthesis of 5-((2,4-dioxo-3,4-dihydropyrido[2,3-d]pyrimidin-1(2H)-yl)methyl)-2-iodobenzoic acid (37)

A solution of compound 36 (3.5 g, 7.0 mmol)) and 6 N HCl (15 mL) in 1,4-dioxane (25 mL) was refluxed for 16 h. The resulting suspension was cooled to RT and NaOH solution was added to adjust to pH 12-13. The solution was stirred for 3 h at room temperature. After completion, the solution was acidified to pH<2.0 by 6 N HCl. The precipitate was filtered, washed with water and small amount of MeOH. The precipitate was dried under reduced pressure to give compound 37 as a white solid.

$^1$H-NMR (400 MHz; DMSO-d6): δ 13.3 (bs, 1H), 11.86 (bs, 1H), 8.66-8.67 (t, 1H, J=4.7), 8.35-8.37 (dd, 1H, J=1.2

Hz, 7.5 Hz), 7.86-7.92 (m, 1H), 7.67 (s, 1H), 7.37-7.32 (m, 1H), 7.16-7.22 (m, 1H), 5.34 (s, 2H), 3.56 (s, 1H), 1.60 (s, 1H).

Yield: (0.96 g, 32%).

ESI-MS: m/z 421.9 $[M-1]^-$.

Synthesis of 1-(3-(4-(cyclopentanecarbonyl)piperazine-1-carbonyl)-4-iodobenzyl) pyrido [2,3-d]pyrimidine-2,4(1H,3H)-dione (TRA-13I)

To a solution of compound 36 (0.2 g, 4.7 mmol) and compound 32 (0.11 g, 5.0 mmol) in DCM was added DIPEA (0.26 mL, 14 mmol) at RT. The resulting mixture was stirred at RT for 15 min, then T3P (50% EtOAc) (0.45 mL, 14 mmol) was added. The reaction mixture was stirred at RT for 16 h. After completion, the RM was diluted with water and extracted with DCM. The organic layer was dried over anhydrous $Na_2SO_4$ and evaporated under reduced pressure. The crude was purified by column chromatography on silica gel (70-80% EtOAc in hexanes) to give compound TRA-13I as a white solid. Yield: (0.16 g, 59%).

ESI-MS: m/z 588.13 $[M+1]^+$.

Example-6

Scheme-9

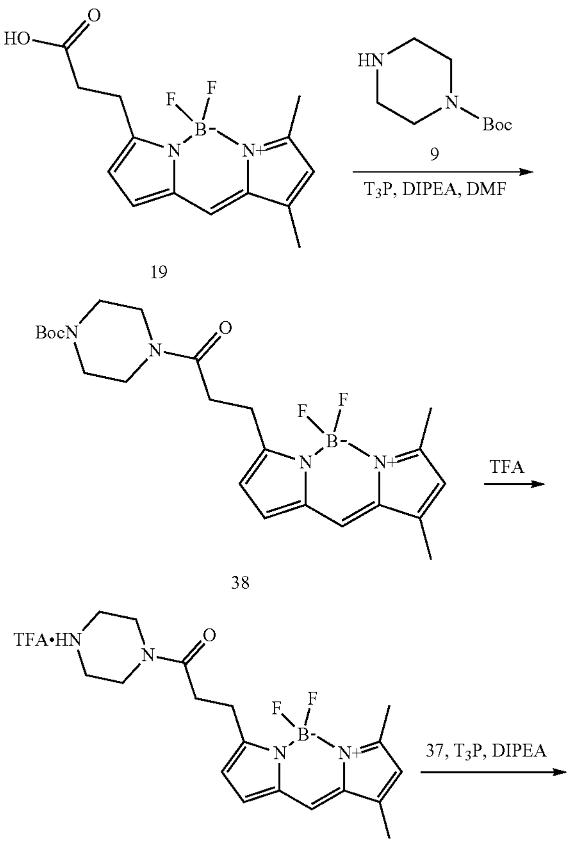

-continued

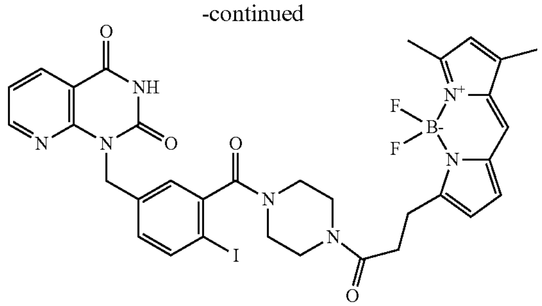

13I-FL

Synthesis of tert-butyl 4-(3-(5,5-difluoro-7,9-dimethyl-5H-5I4,6I4-dipyrrolo[1,2-c:2',1'-f][1,3,2]diazaborinin-3-yl)propanoyl)piperazine-1-carboxylate (38)

To a solution of the compound 19 (1.4 g, 4.7 mmol) and compound 9 (0.9 g, 4.7 mmol) in DCM (15 mL) was added DIPEA (2.5 mL, 14.3 mmol) at RT. The resulting mixture was stirred at RT for 15 min, then $T_3P$ (50% solution in EtOAc) (3.0 mL, 9.6 mmol) was added. The reaction mixture was stirred at RT for 16 h. After completion, the RM was diluted with water and extracted with EtOAc. The organic layer was dried over anhydrous $Na_2SO_4$ and evaporated under reduced pressure. The crude was purified by column chromatography on silica gel (50-70% EtOAc in hexanes) to give compound 38 as a green color gel.

$^1$H-NMR (400 MHz; DMSO-d6): δ 7.69 (s, 1H), 7.08-7.09 (d, 1H, J=3.9 Hz), 6.41-6.42 (d, 1H, J=3.8 Hz), 6.30 (s, 1H), 5.75 (s, 1H), 3.44 (q, 4H), 3.05-3.09 (t, 2H, J=14.2 Hz), 2.71-2.75 (t, 2H, J=15.3 Hz), 2.46 (s, 2H), 2.26 (s, 3H), 1.40 (s, 9H). Yield: (0.9 g, 46%).

ESI-MS: m/z 459.1 $[M-1]^-$.

Synthesis of 3-(5,5-difluoro-7,9-dimethyl-5H-5I4,6I4-dipyrrolo[1,2-c:2',1'-f][1,3,2]diaza borinin-3-yl)-1-(4-(2,2,2-trifluoroacetyl)-4I4-piperazin-1-yl)propan-1-one (39)

To a solution of the compound 38 (0.9 g, 1.9 mmol) in DCM (5 mL) was added TFA (5 mL). The reaction mixture was stirred at RT for 1 h. After completion, the solvents were removed under reduced pressure to give crude material. The crude was purified by column chromatography on silica gel (15-20% MeOH in DCM) to give 39 as a brown solid.

$^1$H-NMR (400 MHz; DMSO-d6): δ 5.37 (s, 2H), 7.20-7.28 (m, 1H), 7.30-7.35 (m, 1H), 7.55-7.62 (m, 1H), 7.85 (d, J=6 Hz, 1H), 8.36 (d, J=7.2 Hz, 1H), 8.69 (d, J=3.6 Hz, 1H), 11.85 (bs, 1H).

Yield: (0.3 g, 42%).

ESI-MS: m/z 359.1 $[M-1]^-$.

Synthesis of 1-(3-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-4-iodobenzyl)pyrido[2,3-d]pyrimidine-2,4(1H,3H)-dione (TRA-13I-FL)

To a solution of the compound 37 (0.2 g, 4.0 mmol) and compound 39 (0.17 g, 4.0 mmol) in DCM (4 mL) was added DIPEA (0.26 mL, 14.0 mmol) at RT. The resulting mixture was stirred to RT for 15 min, then T3P (50% EtOAc) (0.45 mL, 14.0 mmol) was added. The reaction mixture was stirred at RT for 16 h. After completion, the RM was diluted with water and extracted with EtOAc. The organic layer was dried over anhydrous $Na_2SO_4$ and evaporated under reduced pressure. The crude was purified by column chromatography on silica gel (50-70% EtOAc in hexanes) to give compound TRA-13I-FL as a white solid.

Yield: (0.21 g, 58%).

ESI-MS: m/z 765.8 $[M+1]^+$.

Example-7

Scheme-10

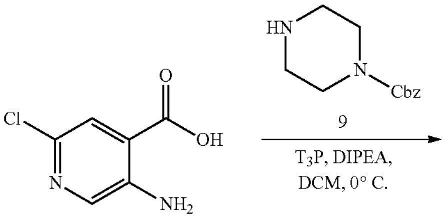

40

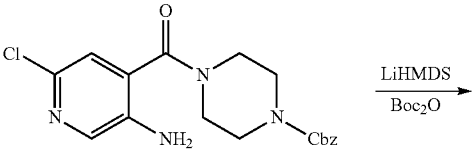

41

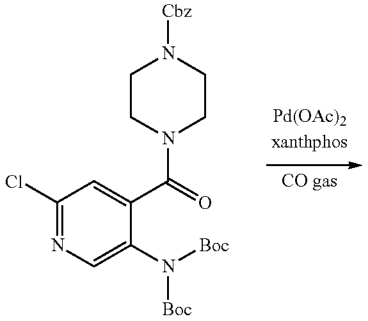

42

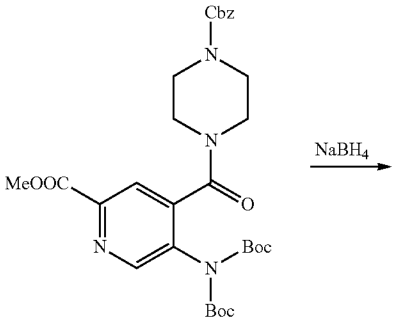

43

-continued

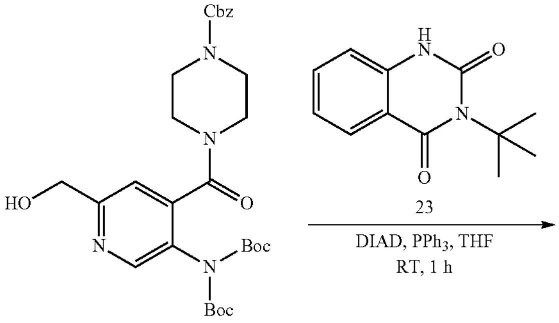

44

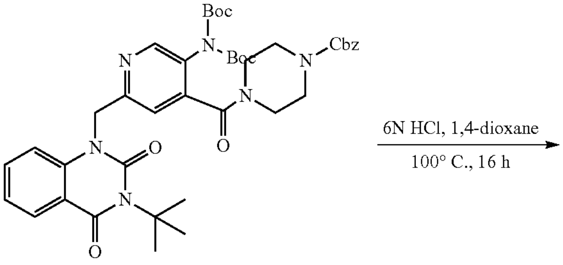

45

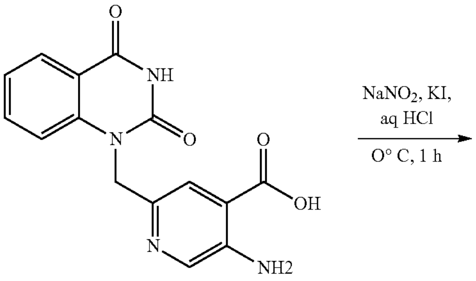

46

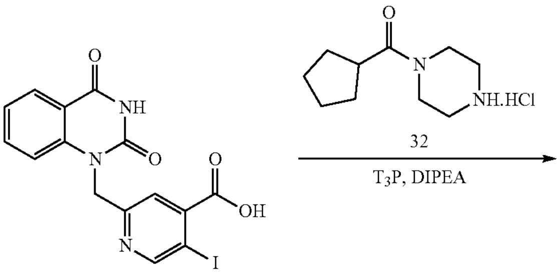

47

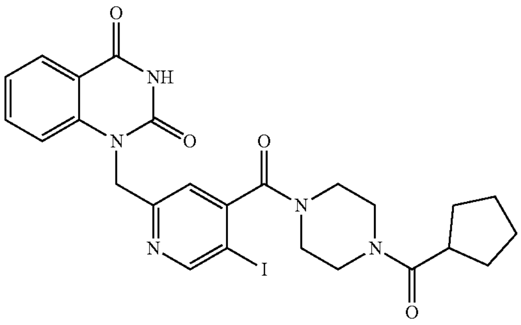

TRA-14I

Synthesis of benzyl 4-(5-amino-2-chloroisonicotinoyl) piperazine-1-carboxylate (41)

To a solution of 40 (10.0 g, 57.9 mmol) and compound 9 (14.0 g, 57.9 mmol) in DCM (100 mL) was added DIPEA (10.2 mL, 57.9 mmol) at RT. The resulting mixture was stirred at RT for 15 min, then T3P (50% EtOAc) (74 mL, 57.9 mmol) was added at 0° C. The reaction mixture was stirred at RT for 16 h. After completion, the mixture was diluted with water and extracted with DCM. The organic layer was dried over anhydrous $Na_2SO_4$ and evaporated under reduced pressure. The crude was purified by column chromatography on silica gel (70-80% EtOAc in hexanes) to give compound 41 as a white solid.

Yield: (12.5 g, 57%).

$^1$H-NMR (400 MHz; DMSO-d6): δ 7.82-7.84 (d, 1H, J=9 Hz), 7.36 (s, 6H), 7.08 (s, 1H), 5.58 (s, 2H), 5.06-5.10 (d, 2H, J=14.1 Hz), 3.38-3.65 (m, 8H).

ESI-MS: m/z 375.4 $[M+1]^+$.

Synthesis of benzyl 4-(5-((bis-(tert-butoxycarbonyl))amino)-2-chloroisonicotinoyl)piperazine-1-carboxylate (42)

To a solution of compound 41 (13.0 g, 34.7 mmol), $Boc_2O$ (15.0 mL, 34.7 mmol) in THE (100 mL) was cooled to −10° C. LiHMDS solution (69.0 mL, 69.4 mmol, 1M in THF,) was added over 15 min below 0° C. The reaction mixture was stirred at 70° C. for 16 h. After completion, the reaction mixture was cooled to 0° C., quenched with sat $NH_4Cl$ solution and extracted with EtOAc. The organic layer was dried over anhydrous $Na_2SO_4$ and evaporated under reduced pressure. The crude was purified by column chromatography on silica gel (70-80% EtOAc in hexanes) to give compound 42 as a white solid. Yield: (16.5 g, 85%).

ESI-MS: m/z 575.4 $[M+1]^+$.

Synthesis of benzyl 4-(5-(bis(tert-butoxycarbonyl) amino)-2-(methoxycarbonyl)isonicotinoyl)piperazine-1-carboxylate (43)

A solution of compound 42 (13.0 g, 27.4 mmol) in DMF (30 mL) and MeOH (30 mL) was purged with argon gas for 10 min, $Pd(OAc)_2$ (0.30 g, 1.37 mmol) and xanthphos (1.58 g, 2.74 mmol) was added. The reaction vessel was filled with CO gas up to 100 psi and stirred in a parr vessel at 80° C. for 16 h. After completion, the RM was filtered through celite pad and washed with EtOAc. The filtrate was washed with water, the organic layer was separated and concentrated under reduced pressure to give crude. The crude material was purified by column chromatography on silica gel (50% of EtOAc in hexane) to afford a desired compound 43 as a white solid.

Yield: (10.0 g, 67%).

$^1$H-NMR (400 MHz; DMSO-$d_6$): δ 8.71-8.73 (d, 1H, J=8.3 Hz), 8.11 (s, 1H), 7.33-7.35 (m, 5H), 5.09 (s, 2H), 3.88 (s, 3H), 3.30-3.50 (m, 6H), 3.17-3.24 (m, 2H), 1.38 (s, 18H).

ESI-MS: m/z 599.5 $[M+1]^+$.

Synthesis of benzyl 4-(5-(bis(tert-butoxycarbonyl) amino)-2-(hydroxymethyl)isonicotinoyl) piperazine-1-carboxylate (44)

A solution of compound 43 (10.0 g, 16.7 mmol) in MeOH (40 mL) was cooled to 0° C., $NaBH_4$ (1.9 g, 50.1 mmol) was added into it portion wise over 10 min. The reaction mixture was stirred at RT for 2 h. After completion, the reaction mixture was quenched with water and extracted with DCM. The organic layer was separated and concentrated under reduced pressure to give a desired compound 44 as a white solid. Yield: (7.0 g, 74%).

ESI-MS: m/z 371.2 $[M+1]^+$.

Synthesis of benzyl 4-(5-(bis(tert-butoxycarbonyl) amino)-2-((3-(tert-butyl)-2,4-dioxo-3,4-dihydroquinazolin-1(2H)-yl)methyl)isonicotinoyl)piperazine-1-carboxylate (45)

A solution of compound 44 (7.0 g, 9.0 mmol) and compound 23 (1.98 g, 9.0 mmol) and $PPh_3$ (3.5 g, 13.6 mmol) in THE at 0° C. was added DIAD (2.8 mL, 13.6 mmol). The reaction mixture was stirred at RT for 1 h. After completion, the reaction mixture was quenched with water and extracted with EtOAc. The organic layer was dried over anhydrous $Na_2SO_4$ and evaporated under reduced pressure, the crude was purified by column chromatography on silica gel (30-40% EtOAc in hexanes) to give compound 45 as a white solid. Yield: (4.0 g, 48%).

$^1$H-NMR (400 MHz; DMSO-$d_6$): δ 8.85 (s, 1H), 8.46 (s, 1H), 7.91-7.93 (d, 1H, J=7.6 Hz), 7.52-7.55 (t, 1H, J=7.6 Hz), 7.44 (s, 1H), 7.32-7.36 (m, 5H), 7.13-7.16 (m, 2H), 5.41 (s, 2H), 5.09)s, 2H), 4.75-4.79 (m, 1H), 3.55 (m, 2H), 3.43 (m, 2H), 3.07 (m, 2H), 1.65 (s, 9H), 1.32 (s, 18H).

ESI-MS: m/z 771.4 $[M+1]^+$.

Synthesis of 5-amino-2-((2,4-dioxo-3,4-dihydroquinazolin-1(2H)-yl)methyl)isonicotinic acid (46)

A mixture of compound 45 (2.0 g, 852 mmol), 6N HCl (5 mL) and 1,4-dioxane (8 mL) was stirred at 100° C. for 16 h. After completion, the reaction mixture was diluted with water, solid suspension was precipitated which was filtered and dried under reduced pressure to give compound 46 as a white solid. Yield: (0.35 g, 41%).

ESI-MS: m/z 311.0 $[M-1]^-$.

Synthesis of 2-((2,4-dioxo-3,4-dihydroquinazolin-1(2H)-yl)methyl)-5-iodoisonicotinic acid (47)

A suspension of compound 46 (0.35 g, 1.1 mmol) in $H_2O$ (20 mL) and $H_2SO_4$ (15 mL) was cooled to 0° C. and $NaNO_2$ (0.155 g, 2.2 mmol) was added. The reaction mixture was stirred at 0° C. for 1 hour, then KI (1.2 g, 7.22 mmol) was added. The mixture was heated to 70° C. for 20 minutes, then cooled back to 0° C. The solid precipitate was filtered, washed with water and dried under reduced pressure to give compound 47 as a light brown solid.

Yield: (0.2 g, 42%).

ESI-MS: m/z 421.2 $[M-1]^-$.

Synthesis of 1-((4-(4-(cyclopentanecarbonyl)piperazine-1-carbonyl)-5-iodopyridin-2-yl)methyl)quinazoline-2,4(1H,3H)-dione (TRA-14I)

To a solution of compound 47 (0.2 g, 0.47 mmol) and 32 (0.095 g, 0.47 mmol) in DMF was added DIPEA (0.26 mL, 1.42 mmol) at RT. The resulting mixture was stirred at RT for 15 min, then $T_3P$ (50% solution EtOAc) (1.0 mL, 1.42 mmol) was added at 0° C. The reaction mixture was stirred at RT for 16 h. After completion, the RM was diluted with water and extracted with DCM. The organic layer was dried over anhydrous $Na_2SO_4$ and evaporated under reduced pressure. The crude was purified by column chromatography on silica gel (70-80% EtOAc in hexanes) to give the target compound TRA-14I as a white solid.

Yield: (0.070 g, 24%).

ESI-MS: m/z 588.20 $[M+1]^+$

B. Specific Compounds of the Invention

B.1. Compounds of the Invention

In the table 1 that are set forth below, exemplary compounds of the invention are set out in tabulated form. In this table, the name of the compound, an arbitrarily assigned compound number and structural information are set out. Although not specifically drawn in the below table, one or more of the indicated halogen atoms may optionally be replaced by a radiolabeled one, such as —F may be replaced by $^{18}F$; I may be replaced by $^{123}I$, . . . .

TABLE 1

| Name | Cpd | Formula |
|---|---|---|
| 1-(3-(4-(cyclopentanecarbonyl)piperazine-1-carbonyl)-4-fluorobenzyl)pyrido[2,3-d]pyrimidine-2,4(1H,3H)-dione | 1 | 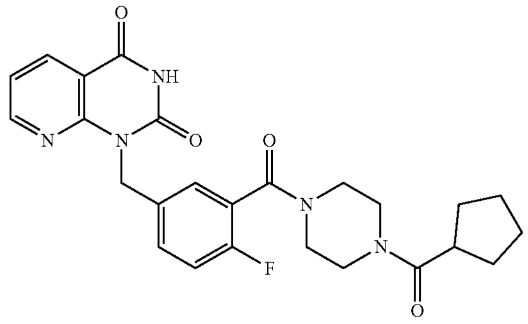 |
| 1-(3-(4-(cyclopentanecarbonyl)piperazine-1-carbonyl)-4-iodobenzyl)pyrido[2,3-d]pyrimidine-2,4(1H,3H)-dione | 2 | 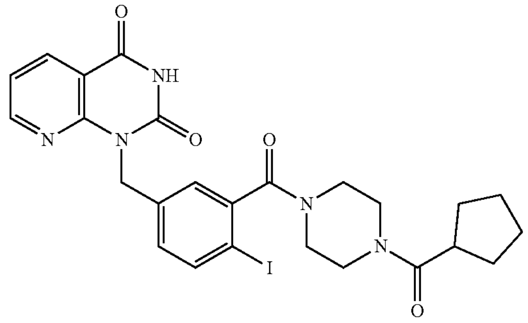 |
| 1-(3-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-4-fluorobenzyl)pyrido[2,3-d]pyrimidine-2,4(1H,3H)-dione | 3 | 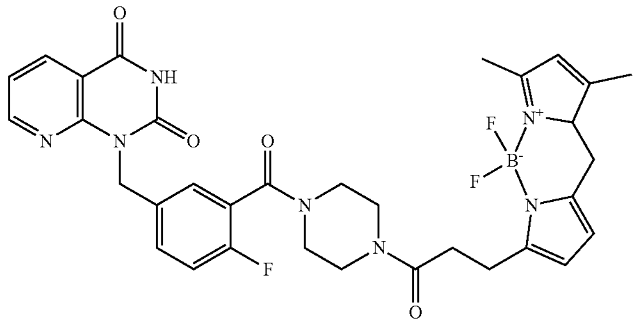 [SMILES: CC1=CC(C)=[N+]2C1Cc1ccc(CCC(=O)N3CCN(C(=O)c4cc(Cn5c(=O)[nH]c(=O)c6cccnc65)ccc4F)CC3)n1[B-]2(F)F] |
| 1-(3-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-4-iodobenzyl)pyrido[2,3-d]pyrimidine-2,4(1H,3H)-dione | 4 | 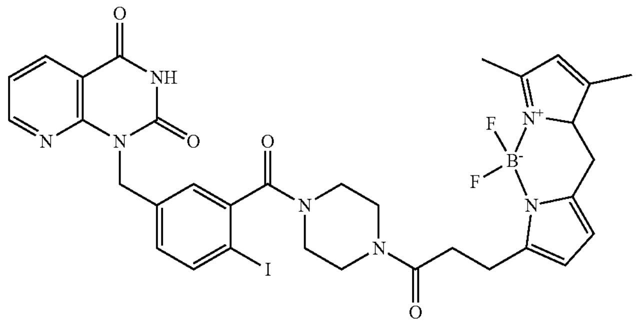 [SMILES: CC1=CC(C)=[N+]2C1Cc1ccc(CCC(=O)N3CCN(C(=O)c4cc(Cn5c(=O)[nH]c(=O)c6cccnc65)ccc4I)CC3)n1[B-]2(F)F] |

TABLE 1-continued

| Name | Cpd | Formula |
|---|---|---|
| 1-((4-(4-(cyclopentanecarbonyl)piperazine-1-carbonyl)-5-fluoropyridin-2-yl)methyl)quinazoline-2,4(1H,3H)-dione | 5 | 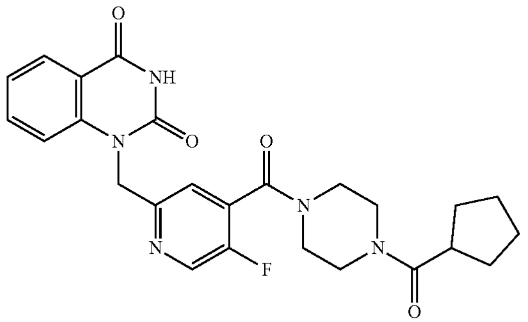 |
| 1-((4-(4-(cyclopentanecarbonyl)piperazine-1-carbonyl)-5-iodopyridin-2-yl)methyl)quinazoline-2,4(1H,3H)-dione | 6 | 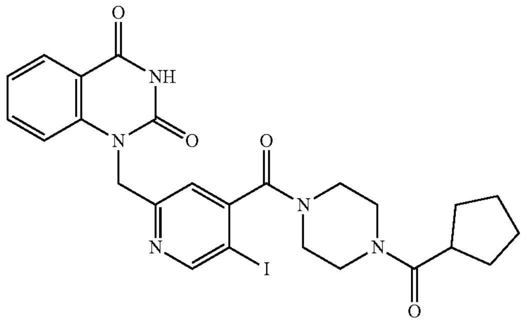 [SMILES: O=C(c1cc(Cn2c(=O)[nH]c(=O)c3ccccc32)ncc1I)N1CCN(C(=O)C2CCCC2)CC1] |
| 1-((4-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-5-fluoropyridin-2-yl)methyl)quinazoline-2,4(1H,3H)-dione | 7 | 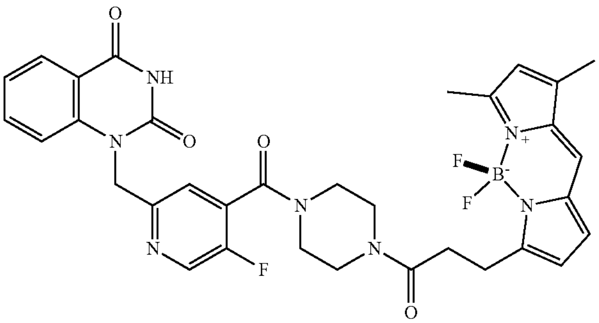 |
| 1-((4-(4-(3-(5,5-difluoro-7,9-dimethyl-5H-5I4,6I4-dipyrrolo[1,2-c:2',1'-f][1,3,2]diazaborinin-3-yl)propanoyl)piperazine-1-carbonyl)-5-iodopyridin-2-yl)methyl)quinazoline-2,4(1H,3H)-dione | 8 | 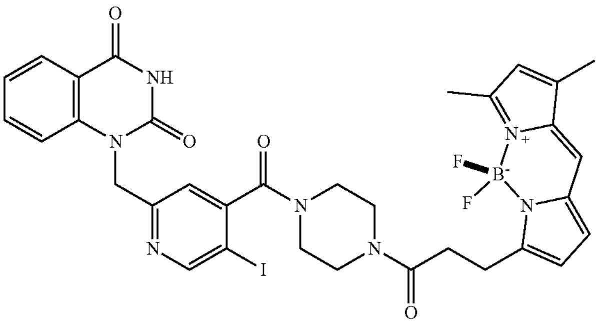 |

Example 5: In Vitro Assay PARP Inhibitory Activity

Materials and Methods

The inhibitors (13F, 14F, 13I-FL, 13F-FL, 14F-FL, 13I and 14I) were kept at −20° C., dissolved in DMSO at 20 mg/mL.

The PARP/Apoptosis Universal Colorimetric Assay Kit 4677-096-K was purchased from BioTechne—R&D Systems. This ELISA kit detects biotinylated poly (ADP-ribose) deposited by PARP-1 onto immobilized histones in a 96-well format. The addition of Strep-HRP (biotin-binding protein) and a colorimetric HRP substrate yields relative absorbance that correlates with PARP-1 activity. The kit is used for in vitro screening of candidate PARP-1 inhibitors and determination of IC50 values.

The protocol recommended by the provider was followed. A 1/10 serial dilution of the inhibitors (ranging from 500 μM to 0.5 nM, 7 data points in triplicate) was added to the designated wells. Wells incubated with 0.5 U/well of PARP-HSA Enzyme without inhibitor were used as the 100% activity reference point. Data was expressed as % of Maximal Activity and plotted in function of the log of concentration (M)) using Graph Pad Prism 8. IC50 values were determined using a dose-response-inhibition equation.

Results

The IC50 of all compounds can be found in Table 1. Best IC50-values were found for 14F and 14F-FL, followed by 13F-FL and 13F.

The Iodine-labelled compounds were found to have a higher IC50 value compared to the Fluorine-labelled compounds.

TABLE 1

IC50-values for different PARP-inhibitors, as calculated by ELISA

| Compound name | Elise test methods April 2020 $IC_{50}$ |
|---|---|
| 13F | ++ |
| 13F-FL | ++ |
| 13I | + |
| 13I-FL | + |
| 14F | +++ |
| 14F-FL | +++ |
| 14I | + |

+++ means < 50 nM, ++ < means 50-500 nM, + means > 500 nM

The dose-response curves for the Fluorine-labelled compounds can be found in FIG. 1. These data confirm the observations of the IC50 values that the 14F and 14F-FL compounds are slightly better compared to the 13F and 13F-FL compounds respectively.

Example 6: In Vitro Cell Uptake Experiments

Since the data presented in example 5 revealed the best IC50 values for the 14F and 14F-FL compounds, the in vitro cell uptake experiments were focused on these specific compounds to test for the functionality/cell penetration capacity and specificity of these fluorescent tracers in the example of head and neck cancer cell lines.

Materials and Methods

Materials

14F-FL as well as the unlabeled analogue 14F were prepared as detailed above. The Olaparib (AZD2461) was purchased from Sigma used as a reference. Stock solutions (20 mg/mL) of the different compounds were prepared in DMSO and kept at −20° C. For further use the compounds were diluted in cell culture media at appropriate concentrations.

The cell lines FaDu (HTB-43, pharynx squamous cell carcinoma) and Cal27 (CRL-2095, tongue squamous cell carcinoma) were purchased from ATCC; the esophageal adenocarcinoma cell lines OE33 was purchased from Sigma.

Cell Culture

FaDu and Cal27 cells were cultured in DMEM culture medium, OE33 were cultured in RPMI culture medium. Media were supplemented with 10% fetal bovine serum, 2 mM L-glutamate, and 100 U/mL penicillin/100 μg/mL streptomycin (non-essential amino acids were also added to DMEM medium). At 80% confluency, cells were trypsinized and sub cultivated at a ratio of 1/20 of 1/20 1/50, twice a week.

In Vitro Cell Binding Study 40 000 cells (FaDu, OE33, or Cal27) were plated in 24-well plates (Cell imaging plates with glass bottom, Eppendorf), and incubated for 2 days at 37° C. After removal of the medium, either 0.5 mL of media (Cond 1), 0.5 mL of 10 μM unlabeled PARPi (14F) (Cond 2) or 0.5 mL of 10 μM Olaparib (Cond 3) was added to the cells. After 30 minutes of incubation at 37° C., cells were washed with 1 mL of medium. Subsequently, 0.5 mL of 14F-FL at a final concentration of 0.1 μM was added and incubated for 15 min at 37° C. The cells were then washed thrice with 1 ml cold PBS, fixed with 1 mL 4% paraformaldehyde (VWR) for 7-10 minutes and washed again with 1 mL PBS. Finally, 0.5 mL of 1 μg/mL DAPI-staining solution (DAPI ready-made solution, Sigma) was added for at least 10 min to stain the cell nuclei.

In Vitro Association Kinetics 40 000 FaDu cells were plated in 24-well plates (Cell imaging plates with glass bottom, Eppendorf), and incubated for 2 days at 37° C. After removal of the medium, 0.5 mL of 14F-FL at a final concentration of 0.1 μM was added and incubated for 2 min, 10 min, 20 min, 30 min, 45 min or 60 min at 37° C. The cells were then washed thrice with 1 ml cold PBS, fixed with 1 mL 4% paraformaldehyde (VWR) for 7-10 minutes and washed again with 1 mL PBS. Finally, 0.5 mL of 1 μg/mL DAPI-staining solution (DAPI ready-made solution, Sigma) was added for at least 10 min to stain the cell nuclei.

In Vitro Dissociation Kinetics 40 000 FaDu cells were plated in 24-well plates (Cell imaging plates with glass bottom, Eppendrof), and incubated for 2 days at 37° C. After removal of the medium, 0.5 mL of 14F-FL at a final concentration of 0.1 μM was added and incubated for 15 min at 37° C. The cells were then washed thrice with 1 ml cold PBS, and further incubated for 0 min, 30 min, 1 h, 2 h, 4 h or 24 h in medium at 37° C. After washing once with 1 mL cold PBS, the cells were fixed with 4% paraformaldehyde (VWR) and staining with DAPI as described above.

Confocal Microscopy

High resolution bright field and fluorescent images of the cells were acquired on a confocal microscope (LSM800, Zeiss) with excitation and emission wavelengths of 405/455 nm for DAPI and 488/525 for BodipyFL (standard conditions). Images were taken with a Plan Apochromat 63×/1.4 oil objective. Images were analyzed with the Software ZenLITE (Zeiss).

Flow Cytometry 250 000 cells (FaDu, Cal27 or OE33) in suspension were incubated with 0.5 mL media, 0.5 mL 10 μM unlabeled 14F or 0.5 mL 10 μM Olaparib-analogue. After 30 min incubation at 37° C., the cells were washed once with 0.5 mL media and subsequently incubated with 0.5 mL 0.1 μM 14F-FL for 10 min at 37° C. The cells were then washed thrice with media (including 1×10 min incubation) and resuspended in FACS buffer (PBS+0.5% FBS+EDTA+$N_3$). Finally, cells were analyzed on a flow cytometer (BD Celesta) in the GFP channel (ex 488 nm, em filter 510 nm). Data was analyzed via FlowJo software.

Results

Cell Binding Studies 14F-FL

Following incubation of 14F-FL with Cal27, FaDu or OE33 cells, an intense green fluorescent signal can be observed in the nuclei of all three cell lines (colocalization with the signal of DAPI, a nuclear stain). The signal of 14F-FL is concentrated within nucleoli; this structure has been described to contain substantial amounts (up to 50%) of the PARP1 enzyme (Boamah, 2012, PLoS Genet). Highest signal is observed in the Cal27 and FaDu cell line, as compared to OE33. When the cells were pretreated with an excess of unlabeled analogue 14F no green fluorescent signal can be seen. (data not shown), demonstrating the specificity of the binding.

Flow Cytometry

Figure 2:
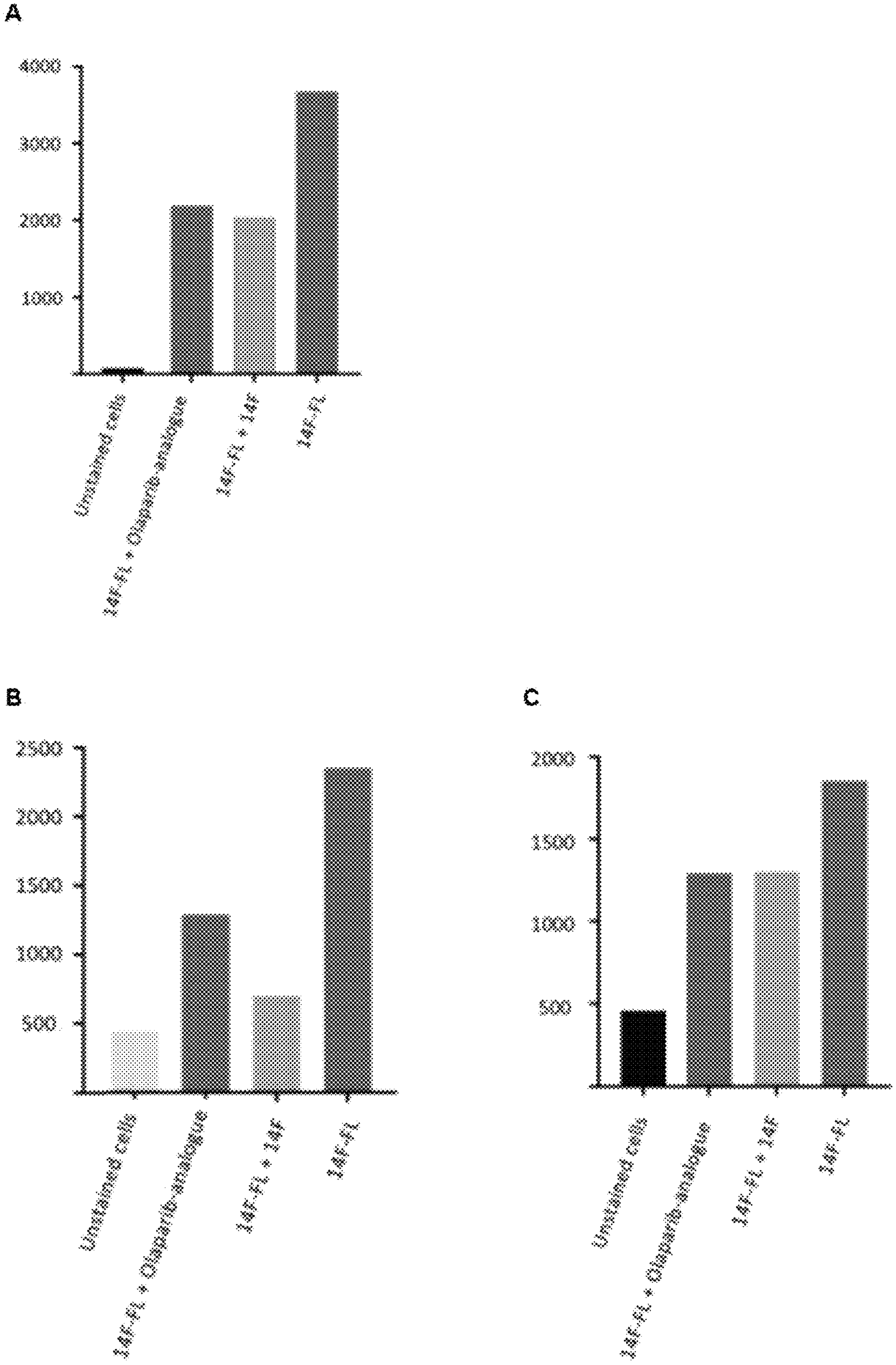
FIG. 2: Flow cytometry data of cell binding by 14F-FL to Cal27 (A), FaDu (B) and OE33 (C) cells.

The flow cytometry data confirm that significant binding can be seen for the 14F-FL compound to Cal27, FaDu and OE33 cells (FIG. 2A-C respectively). This binding is specific, as pretreatment of the cells with an excess of unlabeled 14F, decreased the binding. Of note, the tracer exhibits also some non-specific binding (to the cytoplasm as could be seen on microscopy) since the signal of these 'blocking' conditions is higher than for unstained cells. More intensive washing did not result in less background signal.

Association Kinetics of 14F-FL

Maximal binding of 14F-FL is already achieved within 10 min of incubation with FaDu cells (data not shown). Prolonging the incubation time up to 60 min does not significantly enhance targeting.

Dissociation Kinetics of 14F-FL

After binding, 14F-FL remains bound to its target for a few hours. From about 2-4 h, the signal of 14F-FL in the nucleus gradually decreases. After 24 h, some signal can still be observed in the nuclei, but it is noticeably less (data not shown).

Flow Cytometry

The flow cytometry data confirms the microscopy data described above.

Figure 3:
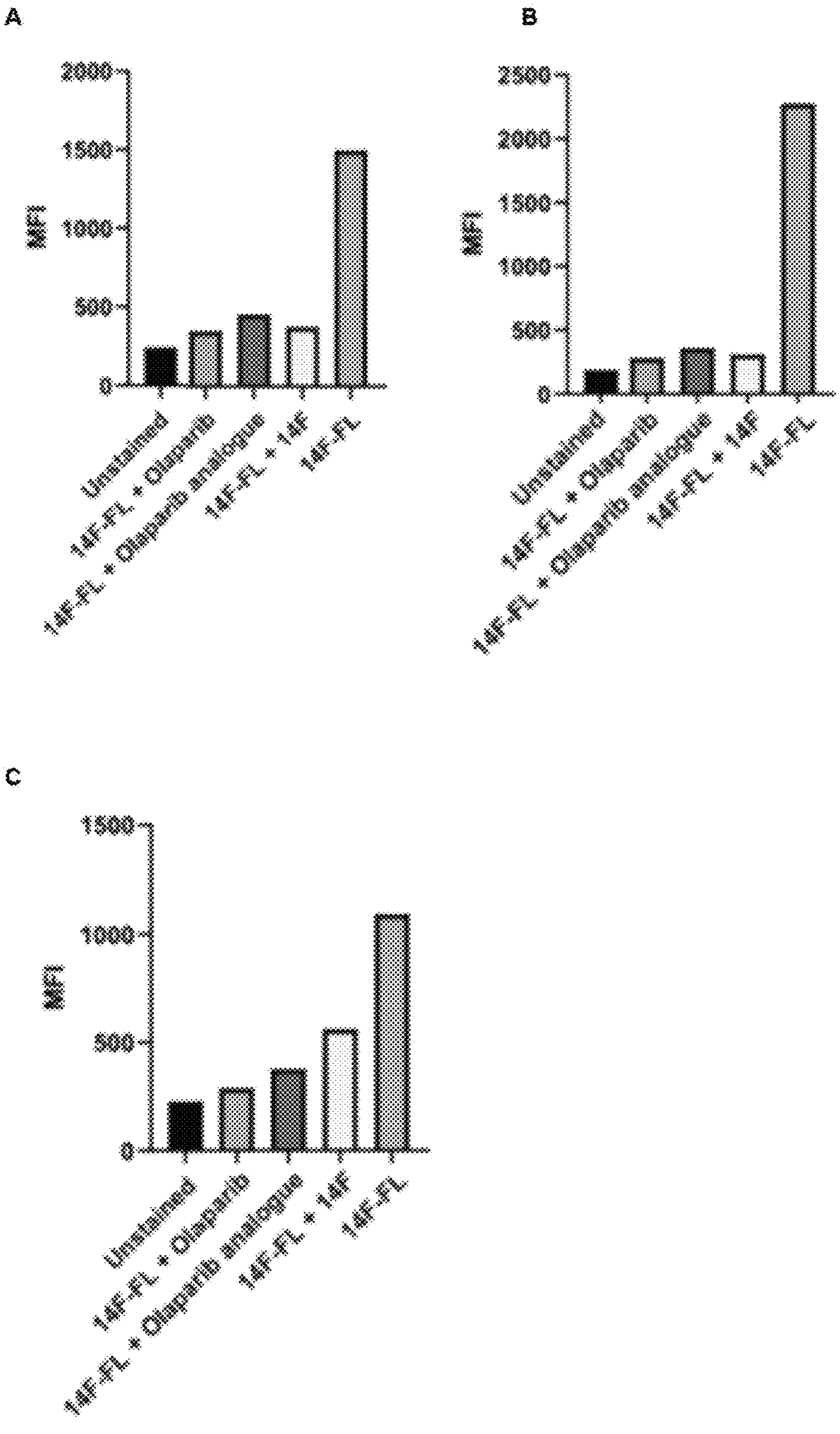
FIG. 3: Flow cytometric analysis of unstained cells and cells incubated with different PARP-inhibitors, FaDu (A), Cal27 (B) and OE33 (C) cells. Cells stained with 14F-FL were used as positive control.

Specifically, significant binding can be seen for the 14F-FL compound (FIG. 3A-C). This binding is specific, as pretreatment of the cells with an excess of unlabeled 14F decreased the binding.

The invention claimed is:

1. A compound of Formula I or a stereoisomer, tautomer, racemate, salt, hydrate, solvate, or isotope thereof, (I)

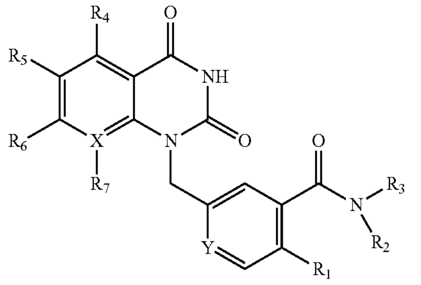

wherein $R_1$ is halogen;

$R_2$ and $R_3$, taken together with the N atom to which they are attached, form a piperazine moiety, which is further substituted with at least one substituent selected from the group consisting of —$C_{1-20}$ alkyl and —C(═O)$R_8$;

wherein $R_8$ is a fluorescent moiety, or at least one of said substituent of $R_2$ and $R_3$ is further substituted with a fluorescent moiety;

$R_4$, $R_5$, $R_6$ and $R_7$ are —H;

X and Y are each independently selected from C or N;

wherein at least one of said X and Y is N;

wherein when X is N then $R_7$ is absent.

2. The compound as defined in claim 1, said compound being of Formula III or a stereoisomer, tautomer, racemate, salt, hydrate, solvate, or isotope thereof, (III)

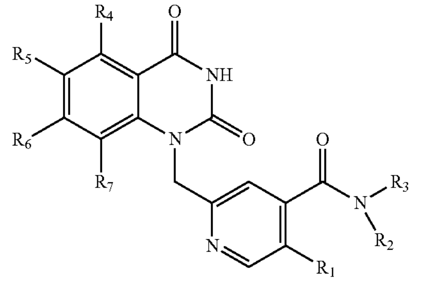

wherein, $R_1$, $R_2$, $R_3$, $R_4$, $R_5$, $R_6$ and $R_7$ are as defined in claim 1.

3. The compound as defined in claim 1, said compound being of Formula II or a stereoisomer, tautomer, racemate, salt, hydrate, solvate, or isotope thereof, (II)

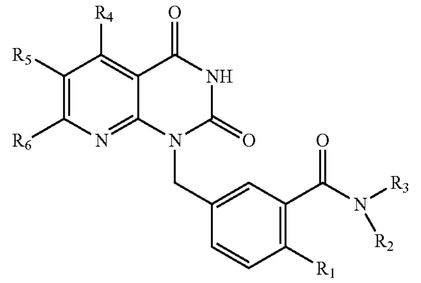

wherein, $R_1$, $R_2$, $R_3$, $R_4$, $R_5$ and $R_6$ are as defined in claim 1.

4. The compound as defined in claim 1;

wherein $R_1$ is a radioactive halogen selected from the group consisting of $^{76}$Br, $^{77}$Br, $^{8}$Br, $^{123}$I, $^{125}$I, $^{131}$I, $^{209}$At, $^{210}$At, and $^{211}$At.

5. The compound as defined in claim 1;

wherein $R_1$ is a radioactive halogen selected from the group consisting of $^{18}$F and $^{123}$I.

6. The compound as defined in claim 1 and being selected from the following list; wherein each Z is independently selected from —I, —Br, —At or —F; each of said —I, —Br, —At and —F being optionally radiolabeled:

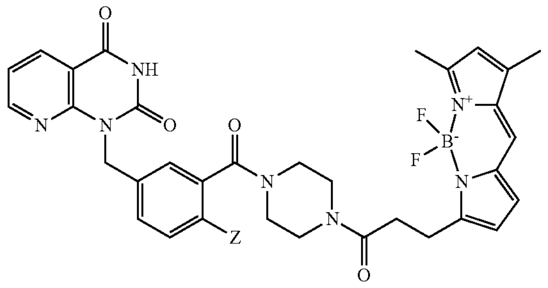

or

-continued

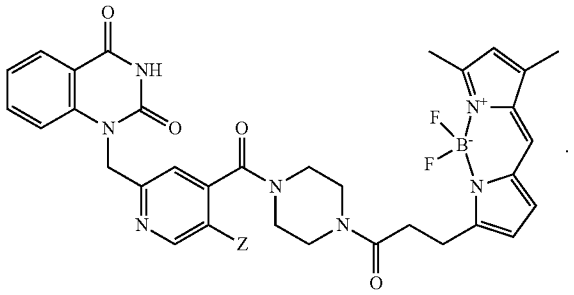

7. The compound as defined in claim 1 and being selected from the following list:

Compound 3

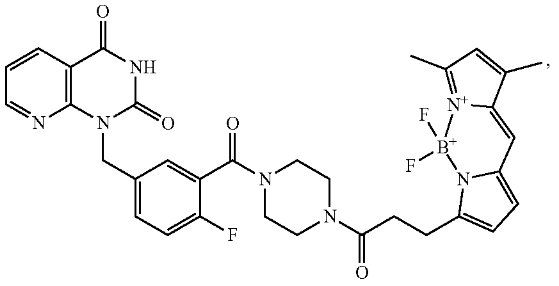

Compound 4

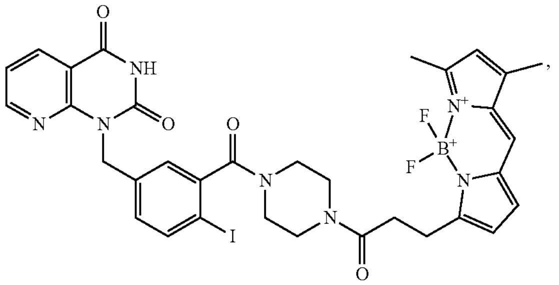

-continued

Compound 7

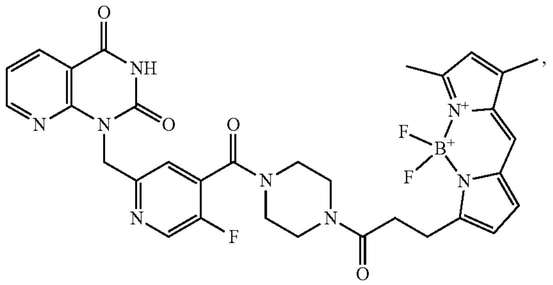

or

Compound 8

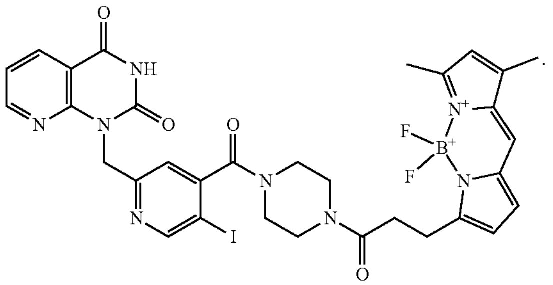

8. A pharmaceutical composition comprising:
(i) the compound as defined in claim 1; and
(ii) a pharmaceutically acceptable diluent, acceptable carrier, excipient, adjuvant or vehicle.

9. A method of treating a disorder characterized by PARP (Poly (ADP-ribose) polymerase) overexpression in a subject in need thereof, comprising administering to the subject the compound as defined in claim 1.

10. The method of claim 9, wherein said disorder characterized by PARP overexpression is a cell proliferative disorder.

11. The method of claim 10, wherein said cell proliferative disorder is selected from the group consisting of breast cancer, ovarian cancer, colorectal cancer, prostate cancer, melanoma, non-small-cell lung cancer, pancreatic cancer, glioblastoma, neuroblastoma, peritoneal cancer, oral carcinoma and esophageal cancer.

* * * * *